US007122533B2

(12) United States Patent
Cushman et al.

(10) Patent No.: US 7,122,533 B2
(45) Date of Patent: *Oct. 17, 2006

(54) COSALANE COMPOUNDS AND METHODS FOR THEIR USE

(75) Inventors: Mark S. Cushman, West Lafayette, IN (US); O. M. Zack Howard, Frederick, MD (US)

(73) Assignees: The United States of America as represented by the Department of Health and Human Services, Washington, DC (US); Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/436,845

(22) Filed: May 13, 2003

(65) Prior Publication Data
US 2003/0212045 A1    Nov. 13, 2003

Related U.S. Application Data

(62) Division of application No. 09/771,769, filed on Jan. 29, 2001, now Pat. No. 6,562,805.

(60) Provisional application No. 60/167,864, filed on Nov. 29, 1999.

(51) Int. Cl.
*A61K 31/56* (2006.01)
*C07J 9/00* (2006.01)

(52) U.S. Cl. ............... 514/169; 514/171; 514/182; 552/506; 552/540; 552/552; 552/565

(58) Field of Classification Search ............. 552/522, 552/525, 505, 540, 506; 514/169, 171, 182
See application file for complete search history.

(56) References Cited

U.S. PATENT DOCUMENTS

| 5,237,110 | A | * | 8/1993 | DeLuca et al. ............. 568/665 |
| 5,246,925 | A | * | 9/1993 | DeLuca et al. ............. 514/167 |
| 5,428,029 | A | * | 6/1995 | Doran et al. ............... 514/167 |
| 5,439,899 | A | * | 8/1995 | Cushman et al. .......... 514/169 |
| 5,484,782 | A | * | 1/1996 | DeLuca et al. ............. 514/167 |
| 5,536,713 | A | * | 7/1996 | Deluca et al. .............. 514/167 |
| 5,587,497 | A | * | 12/1996 | DeLuca et al. ............. 552/653 |
| 6,562,805 | B1 | * | 5/2003 | Cushman et al. .......... 514/169 |
| 2005/0063992 | A1 | * | 3/2005 | Keys ........................ 424/198.1 |
| 2005/0065087 | A1 | * | 3/2005 | Campagnari .............. 514/12 |
| 2005/0065088 | A1 | * | 3/2005 | Thompson ................. 514/12 |
| 2005/0065117 | A1 | * | 3/2005 | Lee ........................... 514/89 |
| 2005/0065126 | A1 | * | 3/2005 | Lee ........................... 514/167 |
| 2005/0065130 | A1 | * | 3/2005 | Thompson ................. 514/167 |
| 2005/0065133 | A1 | * | 3/2005 | Lee et al. .................. 514/167 |
| 2005/0065180 | A1 | * | 3/2005 | Lee ........................... 514/303 |
| 2005/0070512 | A1 | * | 3/2005 | Lee ........................... 514/167 |
| 2005/0119242 | A1 | * | 6/2005 | DeLuca et al. ............. 514/167 |
| 2005/0143358 | A1 | * | 6/2005 | DeLuca et al. ............. 514/167 |

OTHER PUBLICATIONS

Alkhatib et al., "CC CKR5: A Rantes, MIP-1α, MIP-1β receptor as a fusion cofactor for macrophage-tropic HIV-1," *Science* 272:1955-58 (1996).
Choe et al., "The β-chemokine receptors CCR3 and CCR5 facilitate infection by primary HIV-1 isolates," *Cell* 85:1135-48 (1996).
Dean et al., "Genetic restriction of HIV-1 infection and progression to AIDS by a deletion allele of the *CKR5* structural gene," *Science* 273:1856-62 (1996).
Deng et al., "Identification of a major co-receptor for primary isolates of HIV-1," *Nature* 381:661-66 (1996).
Dragic et al., "HIV-1 entry into CD4$^+$cells is mediated by the chemokine receptor CC-CKR-5," *Nature* 381:667-73 (1996).
Gangur et al., "Are chemokines essential or secondary participants in allergic responses?" *Ann. Allergy Asthma, Immunol.* 84:569-81 (2000).
Liang et al., "Identification and characterization of a potent, selective, and orally active antagonist of the CC chemokine receptor-1," *J. Biol. Chem.* 275:19000-08 (2000).
Moore et al., "CXC chemokines mechanism of action in regulating tumor angiogenesis," *Angiogenesis* 2:123-34 (1998).
Murata et al., "Novel palladium(0)-catalyzed coupling reaction of dialkoxyborane with aryl halides: Convenient synthetic route to arylboronates," *J. Org. Chem.* 62:6458-59 (1997).
Ng et al., "Discovery of novel non-peptide CCR1 receptor antagonists," *J. Med. Chem.* 42:4680-94 (1999).
Robinson et al., "Mechanisms of allergic asthma: A Th2 disease," *Lung Biol. Health Dis.* 136:9-41 (1999).
Wang et al., "Human recombinant macrophage inflammatory protein-1α and -β and monocyte chemotactic and activating factor utilize common and unique receptors on human monocytes," *J. Immunol.* 150:3022-29 (1993).
Zlotnik et al., "Recent advances in chemokines and chemokine receptors," *Crit. Rev. Immunol.* 19:1-47 (1999).

(Continued)

Primary Examiner—Sabiha N. Qazi
(74) Attorney, Agent, or Firm—Barnes & Thornburg LLP

(57) ABSTRACT

The present invention relates to methods, compounds and compositions for inhibiting effective binding of a chemokine to its cellular receptor. In one form of the invention, a method includes contacting a cellular population with an effective amount of cosalane or an analog thereof. The invention further relates to methods, compounds and compositions for treating inflammatory diseases. In one form, a method includes administering to a patient a therapeutically effective amount of cosalane or an analog thereof.

32 Claims, 7 Drawing Sheets

OTHER PUBLICATIONS

Casimiro-Garcia et al., "Synthesis and anti-HIV activity of cosalane analogues incorporating nitrogen in the linker chain," *Bioorg. Med. Chem. Lett.* 8:191-200 (2000).

Cushman et al., "Extension of the polyanionic cosalane pharmacophore as a strategy for increasing anti-HIV potency," *J. Med. Chem.* 42:1767-77 (1999).

Cushman et al., "Synthesis of a cosalane analog with an extended polyanionic pharmacophore conferring enhanced potency as an anti-HIV agent," *Bioorg. Med. Chem. Lett.* 8:833-36 (1998).

Cushman et al., "Cosalane analogues with enhanced potencies as inhibitors of HIV-1 protease and integrase," *J. Med. Chem.* 38:443-52 (1995).

Cushman et al., "Design, synthesis, and biological evaluation of cosalane, a novel anti-HIV agent which inhibits multiple features of virus reproduction," *J. Med. Chem.* 37:3040-50 (1994).

Golebiewski et al., "Exploration of the effects of linker chain modifications on anti-HIV activities in a series of cosalane analogues," *Bioorg. Med. Chem. Lett.* 4(10):1637-48 (1996).

Golebiewski et al., "Design and synthesis of cosalane, a novel anti-HIV agent," *Bioorg. Med. Chem. Lett.* 3(8):1739-42 (1993).

Howard et al., "Inhibition of RANTES/CCR-1-mediated chemotaxis by cosalane and related compounds," *Bioorg. Med. Chem. Lett.* 11:59-62 (2001).

Keyes et al., Correlation of anti-HIV potency with lipophilicity in an series of cosalane analogs having normal alkenyl and phosphodiester chains as cholestane replacements, *J. med. Chem.* 39:508-14 (1996).

Keyes et al., "Studies directed toward a more potent cosalene pharmacophore: Synthesis of a substituted tetraphenylethylene which inhibits the cytophatic effect of HIV-1," *Med. Chem. Res.* 39:372-76 (1996).

Paul et al., "Identification of optimal anion spacing for anti-HIV activity in a series of cosalane tetracarboxylates," *Bioorg. Med. Chem. Lett.* 10:2149-52 (2000).

Ruell et al., "Synthesis and anti-HIV activity of cosalane analogues with substituted benzoic acid rings attached to the pharmacophore through methylene and amide linkers," *J. Org. Chem.* 64:5858-66 (1999).

Santhosh et al., "Anti-HIV activity of a series of cosalane amino acids conjugates," *Bioorg. Med. Chem. Lett.* 10:2505-08 (2000).

Kuchimanchi et al., "Intestinal absorption and biodistribution of cosalane and its amino acid conjugates: Novel *anti*-HIV agents," *International. J. Pharmaceutics* 231:197-211 (2002).

\* cited by examiner

COSALANE COMPOUNDS AND METHODS FOR THEIR USE

CROSS-REFERENCE TO RELATED APPLICATIONS

This application is a divisional application of the U.S. national patent application Ser. No. 09/771,769, filed Jan. 29, 2001 now U.S. Pat. No. 6,562,805, which claims priority to U.S. national patent application Ser. No. 09/726,101, filed Nov. 29, 2000, abandoned, which claims priority to U.S. provisional patent application Ser. No. 60/167,874, filed Nov. 29, 1999, which is hereby incorporated in its entirety by reference.

This invention was made with government support under grant number AI 36624 and contract number NO1-CO-56000 awarded by the National Institutes of Health. The Government may have certain rights in this invention.

BACKGROUND OF THE INVENTION

The present invention relates generally to methods, compounds and compositions for inhibiting effective binding of a chemokine to its cellular receptor. The compounds and compositions include cosalane and analogs thereof. The invention further relates to methods, compounds and compositions for treating inflammatory diseases.

Inflammation is a natural immune system response to injury or destruction of tissues and serves to destroy or otherwise confine an injurious agent or injured tissue. The inflammatory process includes targeting immune system and other cells to the site of damage to effect repairs. Although the response is generally protective in nature, in many cases it results in various disease states. A variety of molecules are involved in the inflammation process, including chemokines.

Chemokines are 8–15 Kda secreted chemoattractant proteins that are released by cells at a site of tissue injury and are regarded as important mediators of inflammation due to their ability to enhance migration of certain immune system cells, including, for example, T-cells, B-cells, basophils, neutrophils, and macrophages. Chemokines have been shown to induce directional leukocyte migration (chemotaxis) by binding to seven transmembrane G-coupled protein receptors (8). Chemokines also function to induce other inflammation-related events, including lysosomal enzyme release, respiratory burst, and histamine release. The chemokines and their receptors have been shown to participate in several disease states including allergy and asthma, (9,10) and angiogenesis during solid-tumor development (11). Inhibiting many of these undesired chemokine-induced processes may be beneficial in treating many inflammatory diseases. Compounds, compositions and methods of inhibiting chemokine-induced processes are thus needed. The present invention addresses this need.

SUMMARY OF THE INVENTION

It has been discovered that cosalane and analogs thereof are effective at inhibiting effective binding of a chemokine to its cellular receptor. Accordingly, the present invention provides methods for inhibiting such interactions and compounds and compositions effective for such inhibition.

In one aspect of the present invention, methods of inhibiting binding of a chemokine to its cellular receptor are provided. In one form, a method includes contacting a cellular population with an effective amount of cosalane or an analog thereof as described herein.

In a second aspect of the invention, methods of treating an inflammatory disease are also provided. In one form, a method includes administering to a patient a therapeutically effective amount of cosalane or an analog thereof as described herein. Compositions that include cosalane or analog thereof in combination with an active agent are further provided.

In a third aspect of the present invention, compounds effective in the methods described herein are provided. The compounds include cosalane analogs as described herein.

It is an object of the invention to provide methods and compounds for inhibiting effective binding of a chemokine to its cellular receptor, so that inflammatory or other processes initiated by the chemokines will be inhibited.

It is a further object of the invention to provide methods and compounds for treating an inflammatory disease.

These and other objects and advantages of the present invention will be apparent from the descriptions herein.

DESCRIPTION OF THE PREFERRED EMBODIMENTS

Figure 1:
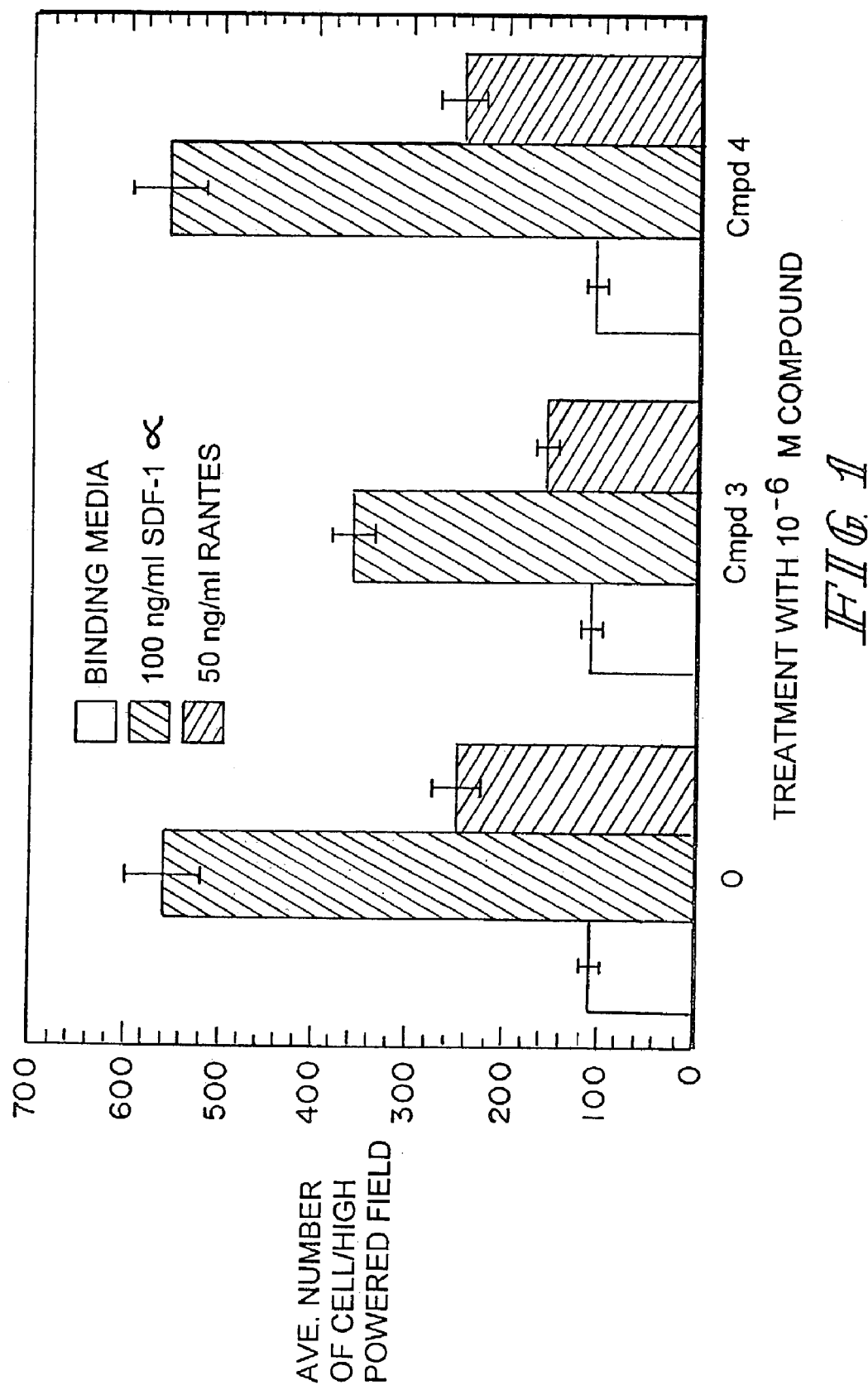
FIG. 1 is a bar graph depicting cosalane analog inhibition of human lymphocyte migration induced by RANTES and SDF1-α as described in Example 1.

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally-occur to one skilled in the art to which the invention relates.

The present invention provides methods for inhibiting effective binding of a chemokine to its cellular receptor and compounds that may advantageously be utilized in the methods of the present invention. Practice of the methods may affect and otherwise inhibit processes initiated or otherwise induced by effective binding of a chemokine to its cellular receptor, including cellular migration and other chemokine-induced events that occur in inflammatory responses described herein and known to the art. The methods may be useful, for example, in treating inflammatory diseases as described below. In one form of the invention, a method of inhibiting effective binding of a chemokine to its cellular receptor is provided that includes contacting a cellular population with an effective amount of cosalane or derivatives or other congeners or analogs thereof. In another form of the invention, compounds are provided that may be effective in inhibiting effective binding of a chemokine to its cellular receptor that include cosalane or derivatives or other congeners or analogs thereof.

In one aspect of the invention, a method for inhibiting effective binding of a chemokine to its cellular receptor includes contacting a cellular population with an effective amount of a compound having the following structure:

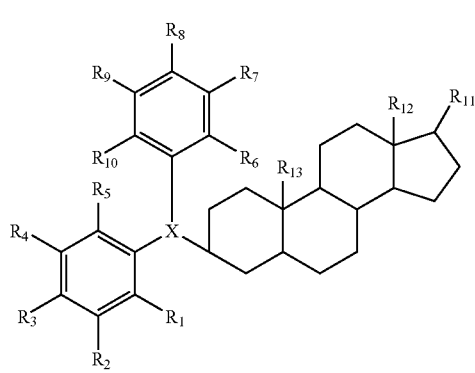

(I)

wherein $R_1$ to $R_{11}$ are independently H, a halogen, hydroxy, amino, alkoxy having 1 to 5 carbon atoms, benzoyloxy, $R_{14}C(O)O$, wherein $R_{14}$ is H or $C_1$–$C_5$ alkyl; COOH or a salt thereof, $SO_3H$ or a salt-hereof, $PO_3H_2$ or a salt thereof, $C_1$–$C_{24}$ alkyl, $COOR_{15}$ where $R_{15}$ is aryl or $C_1$–$C_5$ alkyl; $SO_3R_{16}$, wherein $R_{16}$ is aryl or $C_1$–$C_5$ alkyl; $C(O)NR_{17}R_{18}$ wherein $R_{17}$ and $R_{18}$ are each independently H, $C_1$–$C_5$ alkyl, aryl or hydroxy; $SO_2NR_{19}R_{20}$ wherein $R_{19}$ and $R_{20}$ are each independently H, $C_1$–$C_5$ alkyl or aryl; $SR_{21}$ wherein $R_{21}$ is $C_1$–$C_5$ alkyl or aryl; $SCH_2R_{25}$, wherein $R_{25}$ is aryl; $SC(O)R_{21}$ wherein $R_{21}$ is as defined above; $NR_{22}R_{23}$ wherein $R_{22}$ and $R_{23}$ are each independently H, $C_1$–$C_5$ alkyl or aryl; $NHC(O)$—$R_{24}$, wherein $R_{24}$ is aryl optionally substituted with COOH or a salt thereof, or $C_1$–$C_7$ alkoxy; $O(CH_2)_n$—$R_{26}$—$R_{27}$, wherein n is 1 to 7, $R_{26}$ is aryl, $R_{27}$ is COOH or a salt thereof, $B(OH)_2$ or a salt thereof, nitro, $C_1$–$C_7$ alkoxy or aryl wherein the aryl of $R_{27}$ is substituted with COOH or a salt thereof, $B(OH)_2$ or a salt thereof, nitro or $C_1$–$C_7$ alkoxy; $OC(O)N(H)C(H)(R_{28})COOR_{29}$, wherein $R_{28}$ is an amino acid side chain and $R_{29}$ is H or a $C_1$–$C_4$ alkyl;

$R_{12}$ and $R_{13}$ are $C_1$–$C_7$ alkyl;

X is a ($C_1$–$C_7$ alkylene) or ($C_1$–$C_7$ alkylene)C(O)NH;

or a pharmaceutically acceptable salt thereof.

As known in the art, the term "alkyl" means an aliphatic hydrocarbon which may either be straight chain or branched, and includes, for example, methyl ethyl and structural isomers of propyl, butyl, pentyl, hexyl, heptyl, and octyl. The term alkylene as used herein refers to a saturated or unsaturated hydrocarbon which may be straight chain or branched, and including, for example, methylene, ethylene and structural isomers of propylene, butylene, pentylene and hexylene, heptylene and octylene. The term "aryl" as used herein refers to a group whose molecules have the ring structure characteristic of, for example, benzene, naphthalene, anthracene and fluorene. For example, an aryl group includes phenyl, naphthyl, anthracyl, phenanthryl, fluorenyl and biphenyl.

The halogen group may be selected from halogens known to the art, especially chlorine and bromine. It is further noted that where substituents are indicated, one or more of the indicated substituents may be present.

By "inhibiting effective binding", it is meant that compounds described herein may either inhibit binding of a particular chemokine to its cellular receptor or may allow non-productive binding of a chemokine to its receptor, such as wherein the binding does not promote, induce or otherwise initiate chemokine-induced events, including, for example, cellular chemotaxis and other chemokine-induced events described below and known to the skilled artisan. In certain forms of the invention, the compound may be cosalane, wherein $R_1$ $R_5$, $R_6$ and $R_{10}$ are H, $R_2$ and $R_7$ are chlorine, $R_3$ and $R_8$ are hydroxy, $R_4$ and $R_9$ are COOH or a salt thereof, $R_{11}$ is $CH(CH_3)(CH_2)_3CH(CH_3)_2$, $R_{12}$ and $R_{13}$ are methyl, X is $C=CH(CH_2)_2$, wherein cosalane has the following structure:

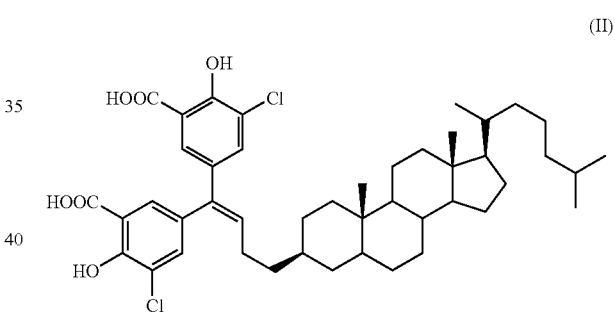

(II)

In other preferred forms of the invention, the hydroxyl group of $R_3$ and/or $R_8$ of cosalane may be replaced with $OCH_2$—$R_{26}R_{27}$, wherein $R_{26}$ is an aryl group, such as a phenyl (Ph) group, and $R_{27}$ may be COOH or a salt thereof. When the aryl group of $R_{26}$ is phenyl, carboxybenzyl analogs of cosalane are formed that may be advantageously utilized in the methods described herein. The phenyl ring of carboxybenzyl may be substituted with the carboxyl group at any available ring position, including the ortho, meta, or para positions, although ortho and meta positions are preferred. Alternatively, a substitutent on the phenyl ring may be nitro ($NO_2$), to form nitrobenzyl derivatives of cosalane or may be $B(OH)_2$ to form boronic acid derivatives of cosalane. The nitro and $B(OH)_2$ groups may also be present at any available ring position, but preferably at the meta position. Furthermore, a substituent on the phenyl ring may be another phenyl ring, preferably at the para position, wherein the phenyl ring substituent may be substituted by COOH or a salt thereof, $B(OH)_2$ or a salt thereof, nitro or a $C_1$–$C_7$ alkoxy group, preferably a methoxy group.

Yet other preferred compounds that may advantageously be utilized in the methods of the present invention include compounds having the following structure:

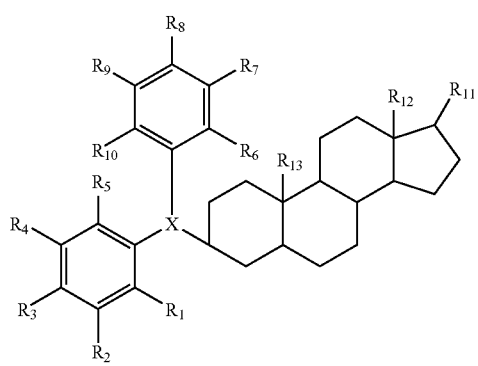

(I)

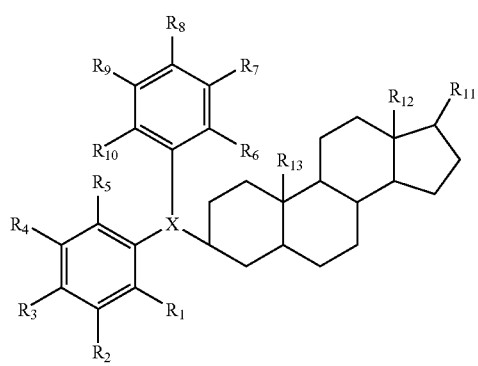

(I)

wherein $R_1$ to $R_{11}$ are independently H, a halogen, hydroxy, amino, alkoxy having 1 to 5 carbon atoms, benzoyloxy, $R_{14}C(O)O$, wherein $R_{14}$ is H or $C_1$–$C_5$ alkyl; COOH or a salt thereof, $SO_3H$ or a salt thereof, $PO_3H_2$ or a salt thereof, $C_1$–$C_{24}$ alkyl, $COOR_{15}$ where $R_{15}$ is aryl or $C_1$–$C_5$ alkyl; $SO_3R_{16}$, wherein $R_{16}$ is aryl or $C_1$–$C_5$ alkyl; $C(O)NR_{17}R_{18}$ wherein $R_{17}$ and $R_{18}$ are each independently H, $C_1$–$C_5$ alkyl, aryl or hydroxy; $SO_2NR_{19}R_{20}$ wherein $R_{19}$ and $R_{20}$ are each independently H, $C_1$–$C_5$ alkyl or aryl; $SR_{21}$ wherein $R_{21}$ is $C_1$–$C_5$ alkyl or aryl; $SCH_2R_{25}$, wherein $R_{25}$ is aryl; $SC(O)R_{21}$ wherein $R_{21}$ is as defined above; $NR_{22}R_{23}$ wherein $R_{22}$ and $R_{23}$ are each independently H, $C_1$–$C_5$ alkyl or aryl; NHC(O)—$R_{24}$, wherein $R_{24}$ is aryl optionally substituted with COOH or a salt thereof, or $C_1$–$C_7$ alkoxy; $O(CH_2)_n$—$R_{26}$—$R_{27}$, wherein n is 1 to 7, $R_{26}$ is aryl, $R_{27}$ is COOH or a salt thereof, $B(OH)_2$ or a salt thereof, nitro, $C_1$–$C_7$ alkoxy or aryl wherein the aryl of $R_{27}$ is substituted with COOH or a salt thereof, $B(OH)_2$ or a salt thereof, nitro or $C_1$–$C_7$ alkoxy; $OC(O)N(H)C(H)(R_{28})COOR_{29}$, wherein $R_{28}$ is an amino acid side chain and $R_{29}$ is H or a $C_1$–$C_4$ alkyl;

wherein at least one of $R_3$ or $R_8$ is $O(CH_2)_n$—$R_{26}$—$R_{27}$, wherein n is 1 to 7, $R_{26}$ is aryl, $R_{27}$ is $B(OH)_2$ or a salt thereof, nitro, $C_1$–$C_7$ alkoxy, or aryl wherein the aryl of $R_{27}$ is substituted with COOH or a salt thereof, $B(OH)_2$ or a salt thereof, nitro or $C_1$–$C_7$ alkoxy;

$R_{12}$ and $R_{13}$ are $C_1$–$C_7$ alkyl;

X is a ($C_1$–$C_7$ alkylene) or ($C_1$–$C_7$ alkylene)C(O)NH;

or a pharmaceutically acceptable salt thereof.

In preferred forms of the invention, $R_1$, $R_5$, $R_6$ and $R_{10}$ are H, $R_2$ and/or $R_7$ are halogen, such as chlorine or bromine, $R_3$ and/or $R_8$ are $O(CH_2)_nR_{26}$—$R_{271}$ wherein n is 1 to 7, $R_{26}$ is a phenyl ring substituted with $R_{27}$, which may be COOH or a salt thereof, $B(OH)_2$ or a salt thereof, nitro or a $C_1$–$C_7$ alkoxy. The phenyl ring may further preferably be substituted with another phenyl ring wherein the phenyl ring substituent may be substituted with COOH or a salt thereof, $B(OH)_2$ or a salt thereof, nitro or a $C_1$–$C_7$ alkoxy.

In yet other preferred forms of the invention, amino acid derivatives of cosalane may be advantageously utilized in the present invention wherein the carboxyl group of $R_4$ and/or $R_9$ of cosalane is conjugated to amino acids, such that at least one of $R_4$ or $R_9$ is $C(O)N(H)C(H)(R_{28})COOR_{29}$, wherein $R_{28}$ is an amino acid side chain and $R_{29}$ is H or a $C_1$–$C_4$ alkyl, and wherein all other R groups are as defined for cosalane. $R_{28}$ may include a wide variety of amino acid side chains, such as the 20 naturally occurring amino acid side chains known to the art, including leucine, glycine, aspartic acid, glutamic acid and alanine. The compounds may have the following structure:

wherein $R_1$ to $R_{11}$ are independently H, a halogen, hydroxy, amino, alkoxy having 1 to 5 carbon atoms, benzoyloxy, $R_{14}C(O)O$, wherein $R_{14}$ is H or $C_1$–$C_5$ alkyl; COOH or a salt thereof, $SO_3H$ or a salt thereof, $PO_3H_2$ or a salt thereof, $C_1$–$C_{24}$ alkyl, $COOR_{15}$ where $R_{15}$ is aryl or $C_1$–$C_5$ alkyl; $SO_3R_{16}$, wherein $R_{16}$ is aryl or $C_1$–$C_5$ alkyl; $C(O)NR_{17}R_{18}$ wherein $R_{17}$ and $R_{18}$ are each independently H, $C_1$–$C_5$ alkyl, aryl or hydroxy; $SO_2NR_{19}R_{20}$ wherein $R_{19}$ and $R_{20}$ are each independently H, $C_1$–$C_5$ alkyl or aryl; $SR_{21}$ wherein $R_{21}$ is $C_1$–$C_5$ alkyl or aryl; $SCH_2R_{25}$, wherein $R_{25}$ is aryl; $SC(O)R_{21}$ wherein $R_{21}$ is as defined above; $NR_{22}R_{23}$ wherein $R_{22}$ and $R_{23}$ are each independently H, $C_1$–$C_5$ alkyl or aryl; NHC(O)—$R_{24}$, wherein $R_{24}$ is aryl optionally substituted with COOH or a salt thereof, or $C_1$–$C_7$ alkoxy; $O(CH_2)_n$—$R_{26}$—$R_{27}$, wherein n is 1 to 7, $R_{26}$ is aryl, $R_{27}$ is COOH or a salt thereof, $B(OH)_2$ or a salt thereof, nitro, $C_1$–$C_7$ alkoxy or aryl wherein the aryl of $R_{27}$ is substituted with COOH or a salt thereof, $B(OH)_2$ or a salt thereof, nitro or $C_1$–$C_7$ alkoxy; $OC(O)N(H)C(H)(R_{28})COOR_{29}$, wherein $R_{28}$ is an amino acid side chain and $R_{29}$ is H or a $C_1$–$C_4$ alkyl;

wherein at least one of $R_4$ and $R_9$ is $OC(O)N(H)C(H)(R_{28})COOR_{29}$, wherein $R_{28}$ is an amino acid side chain and $R_{29}$ is H or a $C_1$–$C_4$ alkyl radical;

$R_{12}$ and $R_{13}$ are $C_1$–$C_7$ alkyl groups;

X is a ($C_1$–$C_7$ alkylene) or ($C_1$–$C_7$ alkylene)C(O)NH;

or a pharmaceutically acceptable salt thereof.

Other preferred compounds useful in the methods of the present invention include those having the following structure:

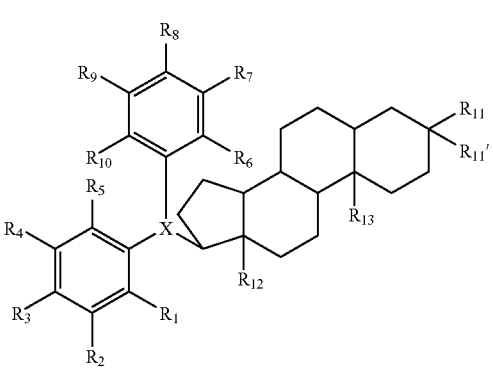

(III)

wherein $R_1$ to $R_{11}$ and $R_{11'}$ are independently H, a halogen, hydroxy, amino, alkoxy having 1 to 5 carbon atoms, benzoyloxy, $R_{14}C(O)O$, wherein $R_{14}$ is H or $C_1$–$C_5$ alkyl; COOH or a salt thereof, $SO_3H$ or a salt thereof, $PO_3H_2$ or a salt thereof, $C_1$–$C_{24}$ alkyl, $COOR_{15}$ where $R_{15}$ is aryl or $C_1$–$C_5$ alkyl; $SO_3R_{16}$, wherein $R_{16}$ is aryl or $C_1$–$C_5$ alkyl; $C(O)NR_{17}R_{18}$ wherein $R_{17}$ and $R_{18}$ are each independently H, $C_1$–$C_5$ alkyl, aryl or hydroxy; $SO_2NR_{19}R_{20}$ wherein $R_{19}$ and $R_{20}$ are each independently H, $C_1$–$C_5$ alkyl or aryl; $SR_{21}$ wherein $R_{21}$ is $C_1$–$C_5$ alkyl or aryl; $SCH_2R_{25}$, wherein $R_{25}$ is aryl; $SC(O)R_{21}$ wherein $R_{21}$ is as defined above; $NR_{22}R_{23}$ wherein $R_{22}$ and $R_{23}$ are each independently H, $C_1$–$C_5$ alkyl or aryl; NHC(O)—$R_{24}$, wherein $R_{24}$ is aryl optionally substituted with COOH or a salt thereof, or $C_1$–$C_7$ alkoxy; $O(CH_2)_n$—$R_{26}$—$R_{27}$, wherein n is 1 to 7, $R_{26}$ is aryl, $R_{27}$ is COOH or a salt thereof, $B(OH)_2$ or a salt thereof, nitro, $C_1$–$C_7$ alkoxy or aryl wherein the aryl of $R_{27}$ is substituted with COOH or a salt thereof, $B(OH)_2$ or a salt thereof, nitro or $C_1$–$C_7$ alkoxy; $OC(O)N(H)C(H)(R_{28})COOR_{29}$, wherein $R_{28}$ is an amino acid side chain and $R_{29}$ is H or a $C_1$–$C_4$ alkyl;

$R_{12}$ and $R_{13}$ are $C_1$–$C_7$ alkyl;

X is a ($C_1$–$C_7$ alkylene) or ($C_1$–$C_7$ alkylene)C(O)NH;

or a pharmaceutically acceptable salt thereof.

In one form of the invention, $R_1$ $R_5$, $R_6$ and $R_{10}$ are hydrogen, $R_2$ and $R_7$ are a halogen such as chlorine or bromine, $R_3$ and $R_8$ are hydroxy, $R_4$ and $R_9$ are COOH or a salt thereof, $R_{12}$ and $R_{13}$ are methyl, X is C=CH(CH$_2$)$_2$ and $_{11}$ and $R_{11'}$ are independently hydrogen or a halogen.

Other preferred compounds useful in the methods of the present invention are those having the following formula:

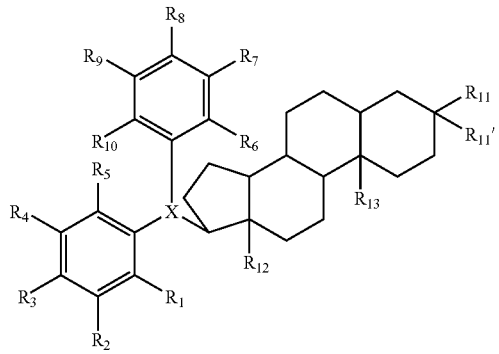

(III)

wherein $R_1$ to $R_{11}$ and $R_{11'}$ are independently H, a halogen, hydroxy, amino, alkoxy having 1 to 5 carbon atoms, benzoyloxy, $R_{14}C(O)O$, wherein $R_{14}$ is H or $C_1$–$C_5$ alkyl; COOH or a salt thereof, $SO_3H$ or a salt thereof, $PO_3H_2$ or a salt thereof, $C_1$–$C_{24}$ alkyl, $COOR_{15}$ where $R_{15}$ is aryl or $C_1$–$C_5$ alkyl; $SO_3R_{16}$, wherein $R_{16}$ is aryl or $C_1$–$C_5$ alkyl; $C(O)NR_{17}R_{18}$ wherein $R_{17}$ and $R_{18}$ are each independently H, $C_1$–$C_5$ alkyl, aryl or hydroxy; $SO_2NR_{19}R_{20}$ wherein $R_{19}$ and $R_{20}$ are each independently H, $C_1$–$C_5$ alkyl or aryl; $SR_{21}$ wherein $R_{21}$ is $C_1$–$C_5$ alkyl or aryl; $SCH_2R_{25}$, wherein $R_{25}$ is aryl; $SC(O)R_{21}$ wherein $R_{21}$ is as defined above; $NR_{22}R_{23}$ wherein $R_{22}$ and $R_{23}$ are each independently H, $C_1$–$C_5$ alkyl or aryl; NHC(O)—$R_{24}$, wherein $R_{24}$ is aryl optionally substituted with COOH or a salt thereof, or $C_1$–$C_7$ alkoxy; $O(CH_2)_n$—$R_{26}$—$R_{27}$, wherein n is 1 to 7, $R_{26}$ is aryl, $R_{27}$ is COOH or a salt thereof, $B(OH)_2$ or a salt thereof, nitro, $C_1$–$C_7$ alkoxy or aryl wherein the aryl of $R_{27}$ is substituted with COOH or a salt thereof, $B(OH)_2$ or a salt thereof, nitro or $C_1$–$C_7$ alkoxy; $OC(O)N(H)C(H)(R_{28})COOR_{29}$, wherein $R_{28}$ is an amino acid side chain and $R_{29}$ is H or a $C_1$–$C_4$ alkyl;

wherein at least one of $R_3$ or $R_8$ is $O(CH_2)_n$—$R_{26}$—$R_{27}$, wherein n is 1 to 7, $R_{26}$ is aryl, $R_{27}$ is $B(OH)_2$ or a salt thereof, nitro, $C_1$–$C_7$ alkoxy, or aryl wherein the aryl of $R_{27}$ is substituted with COOH or a salt thereof, $B(OH)_2$ or a salt thereof, nitro or $C_1$–$C_7$ alkoxy;

$R_{12}$ and $R_{13}$ are $C_1$–$C_7$ alkyl;

X is a ($C_1$–$C_7$ alkylene) or ($C_1$–$C_7$ alkylene)C(O)NH;

or a pharmaceutically acceptable salt thereof.

Other preferred compounds useful in the methods of the present invention are those having the following formula;

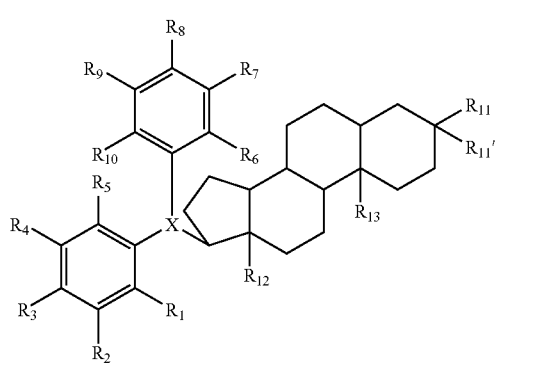

(III)

wherein $R_1$ to $R_{11}$ and $R_{11'}$ are independently H, a halogen, hydroxy, amino, alkoxy having 1 to 5 carbon atoms, benzoyloxy, $R_{14}C(O)O$, wherein $R_{14}$ is H or $C_1$–$C_5$ alkyl; COOH or a salt thereof, $SO_3H$ or a salt thereof, $PO_3H_2$ or a salt thereof, $C_1$–$C_{24}$ alkyl, $COOR_{15}$ where $R_{15}$ is aryl or $C_1$–$C_5$ alkyl; $SO_3R_{16}$, wherein $R_{16}$ is aryl or $C_1$–$C_5$ alkyl; $C(O)NR_{17}R_{18}$ wherein $R_{17}$ and $R_{18}$ are each independently H, $C_1$–$C_5$ alkyl, aryl or hydroxy; $SO_2NR_{19}R_{20}$ wherein $R_{19}$ and $R_{20}$ are each independently H, $C_1$–$C_5$ alkyl or aryl; $SR_{21}$ wherein $R_{21}$ is $C_1$–$C_5$ alkyl or aryl; $SCH_2R_{25}$, wherein $R_{25}$ is aryl; $SC(O)R_{21}$ wherein $R_{21}$ is as defined above; $NR_{22}R_{23}$ wherein $R_{22}$ and $R_{23}$ are each independently H, $C_1$–$C_5$ alkyl or aryl; NHC(O)—$R_{24}$, wherein $R_{24}$ is aryl optionally substituted with COOH or a salt thereof, or $C_1$–$C_7$ alkoxy; $O(CH_2)_n$—$R_{26}$—$R_{27}$, wherein n is 1 to 7, $R_{26}$ is aryl, $R_{27}$ is COOH or a salt thereof, $B(OH)_2$ or a salt thereof, nitro, $C_1$–$C_7$ alkoxy or aryl wherein the aryl of $R_{27}$ is substituted with COOH or a salt thereof, $B(OH)_2$ or a salt thereof, nitro or $C_1$–$C_7$ alkoxy; $OC(O)N(H)C(H)(R_{28})COOR_{29}$, wherein $R_{28}$ is an amino acid side chain and $R_{29}$ is H or a $C_1$–$C_4$ alkyl;

wherein at least one of $R_4$ and $R_9$ is $OC(O)N(H)C(H)(R_{28})COOR_{29}$, wherein $R_{28}$ is an amino acid side chain and $R_{29}$ is H or a $C_1$–$C_4$ alkyl radical;

$R_{12}$ and $R_{13}$ are $C_1$–$C_7$ alkyl;

X is a ($C_1$–$C_7$ alkylene) or ($C_1$–$C_7$ alkylene)C(O)NH;

or a pharmaceutically acceptable salt thereof.

Other preferred compounds include, for example, those represented by formulas IV to X in U.S. Pat. No. 5,439,899.

The compounds of the present invention may be synthesized by the skilled artisan as known in the art. Synthesis of carboxybenzyl derivatives may be accomplished, for example, as described in Paul, G. C. (2000) *Biorg. Med. Chem. Lett.* 10:2149–2152 and Cushman, M. (1998) *Biorg. Med. Chem. Lett.* 8:833–836. Other synthetic routes for the compounds described herein include those found in Cushman et al. (1999) *J. Med. Chem.* 42(10):1767–1777;Ruell, J. A. et al. (1999) 64:5858–5866; and U.S. Pat. No. 5,439,899 to Cushman et al. Amino acid derivatives of cosalane may be synthesized utilizing peptide chemistry known in the art, and as described, for example, in Example 6 and in Santhosh, K. C. et al. (2000) *Bioorg. Med. Chem. Lett.* 10:2505–2508.

A wide variety of chemokine-induced cellular processes may be affected by cosalane and the cosalane analogs described herein, including inflammation-related processes, such as degranulation, respiratory burst, lysosomal enzyme release, histamine release, N-acetyl-beta-glucuronaminidase release, adherence to activated endothelial cells, immune system cell activation, leukotriene release, cellular chemotaxis and chemoattraction.

A wide variety of cells whose chemokine-induced chemotaxis may is be inhibited by cosalane and analogs thereof include immune system cells, such as granulocytes, including neutrophils, polymorphonuclear cells, eosinophils, and basophils, lymphocytes, including B and T cells, natural killer cells, and monocytes. Other immune system cells whose chemokine-induced migration may be affected include dendritic cells and mast cells.

Other cells performing various processes that may be affected by cosalane or analogs thereof include, for example, stem cells, keratinocytes, endothelial cells, melanoma cells, and fibroblasts. Chemokine-induced processes performed by these cells that may be affected by cosalane or analogs thereof include, for example, proliferation (e.g., involving endothelial cells and keratinocytes), growth inhibition (e.g., involving stem cells), adhesiveness and haptotactic response (e.g., involving melanoma cells) and angiogenesis (e.g., involving endothelial cells).

The chemokines that affect the various processes described herein include, for example, members of the CXC (alpha-intercrines), CC (beta-intercrines, C and CXXXC classes. Members of the CC chemokine class include, for example, RANTES, MCP, including MCP-1, MCP-2, MCP-3 and MCP-4, eotaxin, MDC, TARC, MIP-1α, and HCC-1. Members of the CXC class include, for example, PF4, IL-8, GRO-alpha, ENA-78, IP-10, BCA-1, ITAC and SDF-1. Members of the C class include lymphotactin and members of the CXXXC class include fractalkine. In preferred forms of the invention, cosalane or analogs thereof affect the processes controlled, regulated or otherwise caused by members of the CC class of chemokines, such as RANTES or eotaxin. In other preferred forms of the invention, cosalane or analogs thereof affect the processes controlled, regulated or otherwise caused by members of the CXC class of chemokines, such as SDF-1α.

The methods described herein may be utilized in vitro or in vivo. When utilized in vivo, the methods may be advantageous in treating inflammatory diseases. A method of treating an inflammatory disease may include administering to a patient a therapeutically effective amount of any of the compounds described above. The patient is preferably an animal, such as a mammal, and further preferably a human.

A wide variety of inflammatory diseases may be treated with cosalane and analogs thereof described herein, such as inflammatory conditions that may be mediated by, or otherwise involve, chemokines, including acute inflammatory diseases as well as chronic inflammatory diseases. Inflammatory diseases that may be treated include, for example, pathogenic infections such as leischmaniasis, and other pathogenic infections caused by, for example, bacteria, fungi, and protozoans, solid tumor development, granuloma formation, allergies, asthma, arthritis, atheroscerlosis, uvitis of the eye, acute renal failure and other known inflammatory diseases in the art.

The compounds may be administered to a patient by a variety of routes, including oral and nasal, including by aerosol therapy using metered does inhalers and/or nebulizers, rectal, transdermal, ocular, subcutaneous injection and parenteral, including intravenous administration. It is realized that the compounds may be administered by a combination of different routes, although in certain circumstances, certain routes may be more preferred.

The compounds of the present invention may be administered in a pharmaceutically acceptable carrier. The carrier may be selected according to the route of administration. The carrier may include a liquid that is suitable, for example, for oral administration, including water, saline or other aqueous or other solution or beverage. The carrier may be selected for parenteral administration, and may include a sterile aqueous or non-aqueous solution that may include preservatives, bacteriostats, buffers and antioxidants known to the art. The compounds may be combined with an aerosol formulation to be administered, for example, by inhalation through the nose or mouth. The compounds may further be formulated into tablets, capsules or other orally-acceptable carriers. Tablets may include, for example, one or more of lactose, mannitol, corn starch, potato starch, microcrystalline cellulose, acacia, gelatin, colloidal silicon dioxide, talc, magnesium stearate, stearic acid, and other known excipients, colorants, diluents, buffering agents, and preservatives. Methods of preparing such carriers are well known to the skilled artisan.

The amount of the compound that will be therapeutically effective will depend on a variety of factors, including the nature and extent of the disease or other inflammatory condition being treated, the potency or activity of the active ingredient (e.g., cosalane or analog thereof) utilized, and the route of administration. The skilled artisan will be able to determine the optimum dosage by routine experimentation. A typical dose, in mg compound per kg body weight typically ranges from about 0.01 mg/kg to about 100 mg/kg, preferably about 0.1 mg/kg to about 15 mg/kg, but further preferably ranges from about 1 mg/kg to about 10 mg/kg.

Compositions are also provided herein that include the compounds described herein and another active agent. As used herein, the term "active agent" refers to other agents that may help reduce inflammation or provide some other desired benefit. Suitable active agents include, for example, non-steroidal antiinflammatory drugs, such as aspirin, ibuprofen and COX-2 inhibitors; steroids, such as prednisone, and progesterone; ureido-derivatives of poly-4-amino-2-carboxyl-1-methyl pyrrole, including suradista and related compounds, gold and leukotriene antagonists. The amount of a particular agent included in the compositions will depend on a variety of factors, including the nature and extent of the disease being treated, the activity or potency of the cosalane analog, and the nature of the active agent. However, the agents are typically included in the composition in therapeutically effective amounts, such as in a weight ratio of cosalane compound or analog to active agent of about 1:10, preferably about 1:1 and further preferably about 10:1.

Reference will now be made to specific examples illustrating the compositions and methods above. It is to be understood that the examples are provided to illustrate preferred embodiments and that no limitation to the scope of the invention intended thereby.

EXAMPLES 1–5

Materials and Methods

Unless otherwise indicated, all chemicals were purchased from Sigma Chemical Co. (St. Louis, Mo.). Chemokines were purchased from the NIH cytokine repository.

Human embryonic kidney cells 293 (HEK-293) transfected to express human CCR1, $CCR_3$, or CCR5 receptors were cultured in Dulbecco's Modified Eagles Medium (DMEM, Biowhiftaker, Walkersville, Md.) containing 10% Fetal Bovine Serum (FBS, Hyclone, Logan, Utah), 2 mM glutamine and 100 U/ml penicillin and streptomycin (Quality Biologicals, Gaithersburg, Md.). Peripheral blood mononuclear cells were isolated from fresh normal donor apheresis packs by centrifugation over Ficoll. Monocytes were enriched by 85–95% using percoll fractionation (Pharmacia, Piscataway, N.J.).

Chemotaxis Experiments

Monocyte chemotaxis was performed as previously described [Wang (1993) J. Immunol. 150:3022–3029]. Briefly, monocytes were resuspended in binding media (RPMI-1640 media containing 1% BSA, 25 mM HEPES, pH 8.0) at $1-2\times10^6$ cells/ml. Chemokines, diluted in binding media, were mixed with cosalane or the indicated cosalane analog and placed in the lower wells of a micro-chemotaxis chamber (Neuro Probe, Cabin John, Md.). Five micrometer polyvinyl-free polycarbonate membranes were placed over the chemokine mixtures. After the micro-chemotaxis chamber was assembled, 50 µl of cells were placed in the upper wells. The filled chemotaxis chambers were incubated in a humidified $CO_2$ incubator for 90 minutes.

After incubating, the membranes were removed from the chemotaxis chamber assembly followed by gently removing the cells from the upper side of the membrane. Then cells on the lower side of the membrane were stained.

The number of cells migrating to the chemokine mixtures was determined for binding media alone, and chemokine treated and untreated cells. HEK-293 cells transfected to express human CCR1, $CCR_3$ or CCR5 receptors were resuspended in binding media at $7.5\times10^5$ cells/ml. Ten µm polyvinyl-free polycarbonate membranes (Neuro Probe) were treated with 47 ug/ml rat tail collagen type 1 (Collaborative Biomedical Products, Bedford, Md.) in RPMI-1640 overnight, dried and placed over the chemoattractants. The assembled chemotaxis chambers were incubated in a humidified $CO_2$ incubator for 5.5–6 hours. After the incubation, the membranes were removed from the chemotaxis chamber assembly followed by gently removing cells from the upper side of the membrane. The stained and dried membrane was mounted and the cells on the underside of the membrane were counted at 200× magnification. The results are reported as the average number of cells per high powered field at a given chemokine concentration±standard deviation.

Cosalane Analogs Tested

The compounds examined in the present study included cosalane (compound 1), a series of benzyl ether derivatives 2–11, and a number of amino acid conjugates 12–16, wherein compounds 2–11 have the following structure:

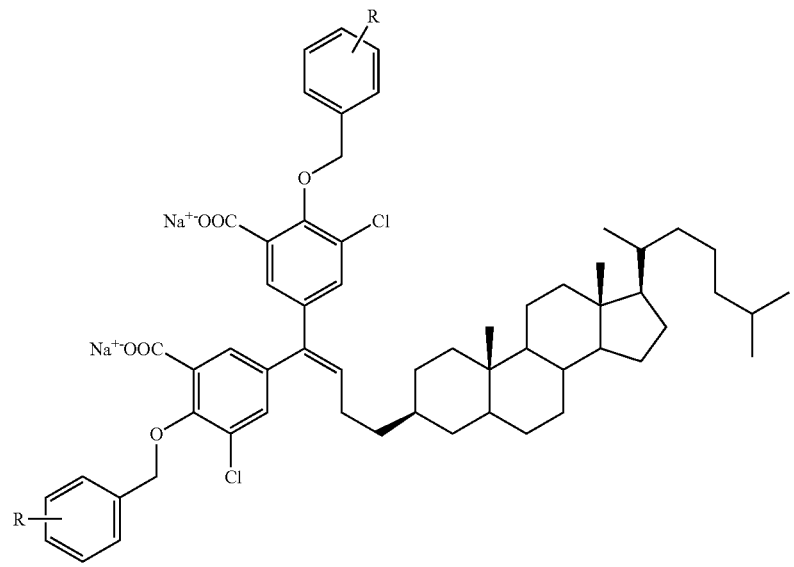

wherein R is, for compound 2, m-$COO^-Na^+$; for compound 3, o-$COO^-Na^+$; for compound 4, p-COOH; for compound 5, p-$COO^-Na^+$; for compound 6, p-(m-PhCOOH); for compound 7, m-$NO_2$; for compound 8, p-$BO_2H^-Na^+$; for compound 9, m-$BO_2H^-Na^+$; for compound 10, o-$BO_2H^-Na^+$; for compound 11, o-$OCH3$, p-COOH.

Compounds 12–16 have the following structure:

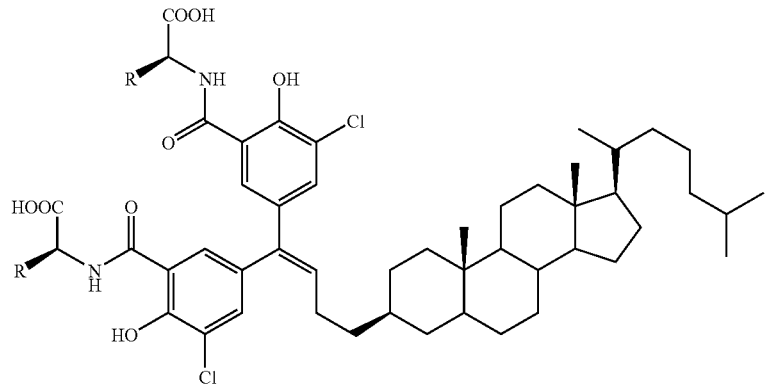

wherein R is, for compound 12, H; for compound 13, CH$_2$COOH; for compound 14, CH$_2$CH$_2$COOH; for compound 15, CH$_2$CH$_2$SCH$_3$; for compound 16, CH$_2$Ph.

Figure 7:
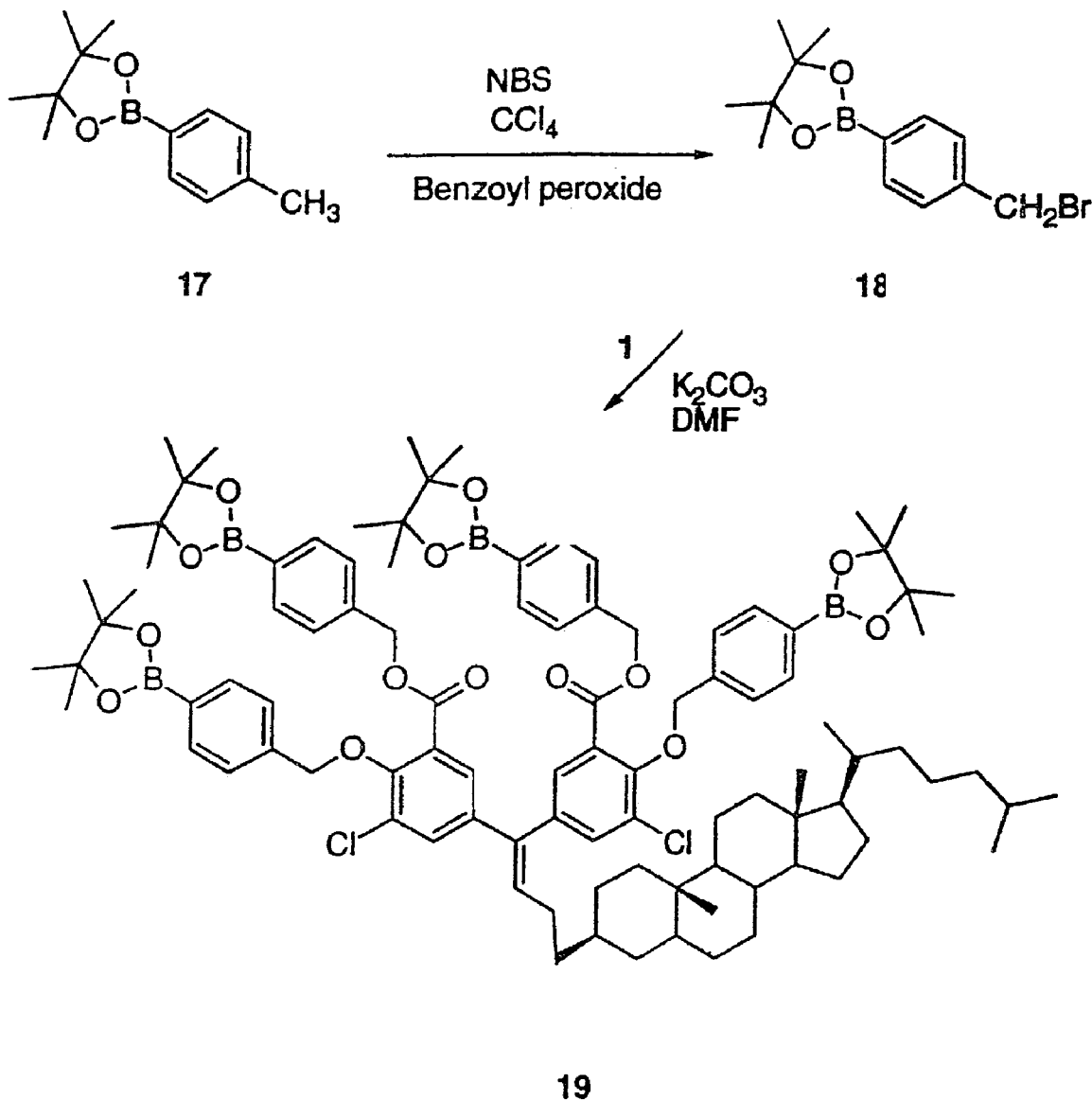
FIG. 7 depicts selected steps in the formation of phenylboronic acid conjugates of cosalane.

Syntheses of the carboxybenzyl derivatives 2–5, the m-nitrobenzyl analog 7, and the biphenyl derivative 6 from cosalane (compound 1) and protected benzyl bromides were previously reported (12–14) and the synthesis of the benzyl congener 11 was performed by straightforward modification of the published routes. Referring to FIG. 7, the sodium salt 8 of the p-benzylboronic acid derivative was synthesized by benzylic bromination of 4,4,5,5-tetramethyl-2-p-tolyl-1,3,2-dioxaborolane 17 (15) with NBS in CCl$_4$ in the presence of benzoyl peroxide at reflux for 24 hours to afford the corresponding benzyl bromide 18, followed by reaction of 18 with cosalane (compound 1) in DMF with potassium carbonate as the base at room temperature for 24 hours to yield intermediate 19. Treatment of 19 with K$_2$CO$_3$ in aqueous EtOH, followed by Na$_2$CO$_3$ in aqueous EtOH, provided the desired product 8. The corresponding meta and ortho boronic acid salts 9 and 10 were synthesized similarly. The syntheses of the amino acid conjugates 12–14 and 16 have also been reported, and 15 was obtained by similar peptide chemistry (16).

EXAMPLE 1

Effect of Cosalane on SDF-1α- and RANTES-induced Migration of Human Monocytes or Lymphocytes The initial hypothesis to be tested was that cosalane would bind to chemokines and thereby inhibit chemokine-induced cell migration. The ability of cosalane to block SDF-1α (a CXCR4 ligand) and RANTES- (a CCR1, CCR3, and CCR5 ligand) induced migration of human monocytes or lymphocytes was therefore examined.

The ability of the cosalane analogs 3 and 4 to block SDF-1α (a CXCR4 ligand) and RANTES (a CCR1, CCR3, and CCR5 ligand) induced migration of human monocytes or lymphocytes was initially evaluated. In these experiments, cosalane analogs 3 and 4 were mixed with the indicated concentrations of either RANTES or SDF-1α prior to their being placed in the lower wells of the chemotaxis chamber. Both 3 and 4 were screened at a concentration of 1 μM. The results in FIG. 1 show that the bis(o-carboxybenzyl) compound 3 was an effective inhibitor of both RANTES-induced and SDF-1α-induced monocyte migration, but the bis(p-carboxybenzyl) analog 4 was inactive. These relative potencies are the reverse of what was previously seen in anti-HIV assays in which compound 4 proved to be an inhibitor of fusion and attachment (13).

The ability of other CCR1 and CCR5 ligands (at 2.5 ng/ml) to be inhibited by the cosalane analogs 2, 3, 4, and 5 (all tested at a concentration of 1 μM) was tested. Surprisingly, neither MiP1-α- nor MIP1-β-induced monocyte migration was inhibited by compounds 3, 4, and 5, while congener 2 proved to be a very weak inhibitor of MIP1-β that induced less than 10% reduction in cell numbers (data not shown). MIP1-α migration was not reduced by compound 2 (data not shown). It is noted that both MIP1-α and MIP1-β are ligands for CCR1, CCR5, and D6 (8).

EXAMPLE 2

Figure 2:
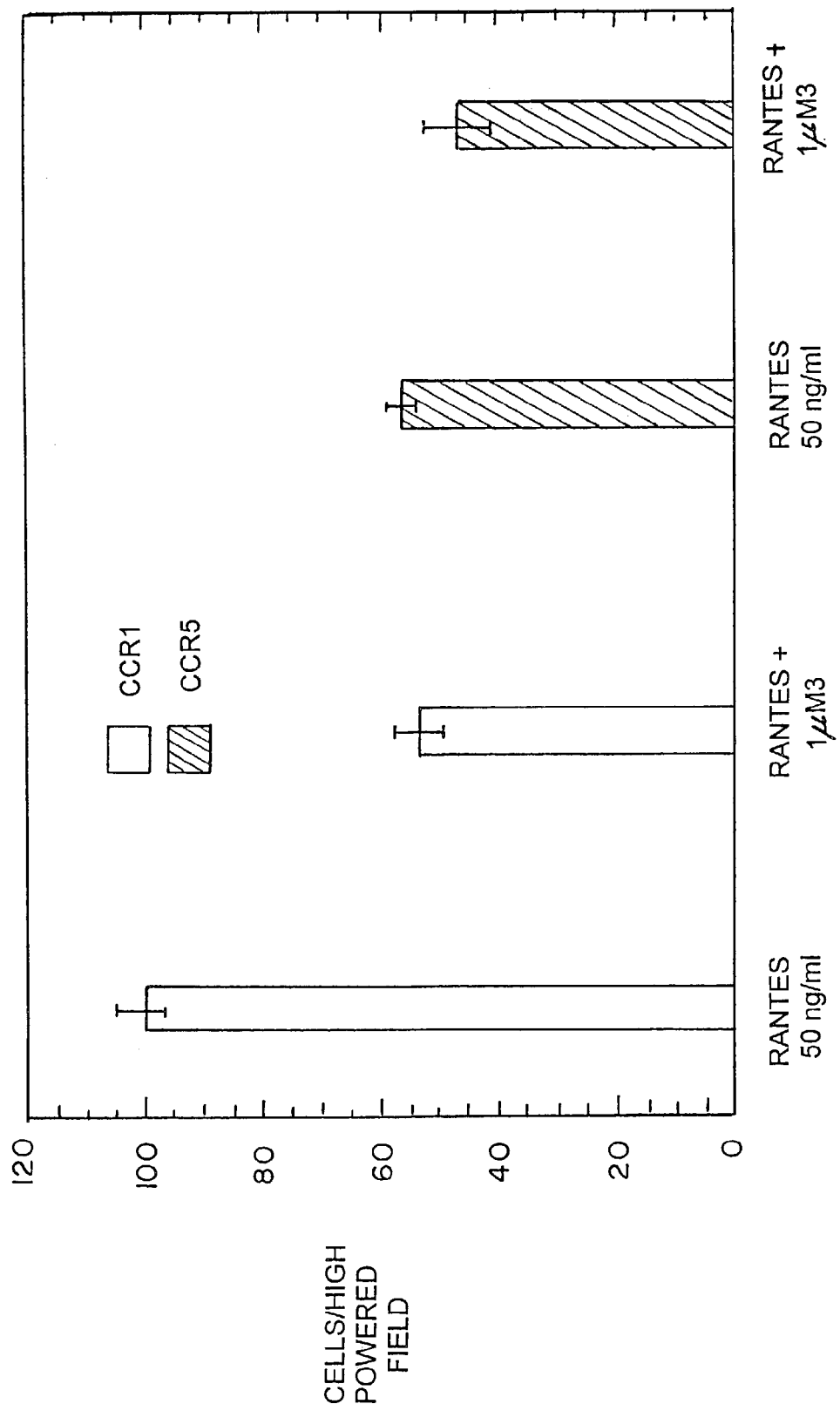
FIG. 2 is a bar graph depicting the inhibitory effect of a cosalane analog on RANTES-induced CCR1-HEK-293 (human embryonic kidney cell line 293) transfectant migration but not RANTES-induced CCR5/HK-293 transfectant migration as described in Example 2. CCR1 and CCR5 are receptors for the CC class of chemokines.

Effect of Cosalane Analogs on RANTES-induced Monocyte Migration and RANTES-induced Migration of Human Embryonic Kidney Cells Transfected to Express the CCR1 or CCR5 Receptor The ability of compound 3 to inhibit RANTES-induced migration of human embryonic kidney (HEK) cells transfected to express individual chemokine receptors was initially tested. Although the cosalane analog 3 (1 μM) had no effect on RANTES-induced migration of CCR5 transfectants, it inhibited 50% of RANTES-induced CCR1 transfectant migration (FIG. 2). In contrast, the MIP1α- and MIP1β-induced migration of CCR1 transfectants was not inhibited by compounds 1, 2 or 3 when tested at concentrations of 1 μM (data not shown). Although not being limited by theory, these studies suggested that the cosalane analog 3 was acting as a selective inhibitor of the RANTES-CCR1 and SDF-1α-CXCR4 interactions.

Cosalane and a wider range of cosalane analogs 2–16 were then evaluated as inhibitors of both RANTES-induced monocyte migration and RANTES-induced CCR1/HEK migration. The results of these studies are shown in Table 1.

TABLE 1

Inhibition of RANTES-induced monocyte and CCR1/HEK migration by cosalanes.[a]

| Compd[b] | IC$_{50}$ (μM) RANTES-Induced Monocyte Migration | IC$_{50}$ (μM) RANTES-Induced CCRI/HEK Migration |
|---|---|---|
| 1 | 0.76 | 0.26 |
| 2 | 10 | 10 |
| 3 | 3.9 | 0.26 |
| 4 | NA[c] | NT[d] |
| 5 | NA[c] | NA[c] |
| 6 | 3.0 | 9.1 |
| 7 | 3.5 | 5.7 |
| 8 | NA[c] | NT[d] |
| 9 | 2.2 | 4.0 |
| 10 | NA[c] | Nt[d] |
| 11 | NA[c] | NT[d] |
| 12 | 0.37 | 10 |
| 13 | NA[c] | NT[d] |
| 14 | NA[c] | NT[d] |
| 15 | 0.82 | 12.7 |
| 16 | NA[c] | NT[d] |

[a]There was ≦ 5% standard error in the IC$_{50}$ values.
[b]See references 1, 13, 14 and 16 for anti-HIV activites.
[c]Not active.
[d]Not tested Considering the benzyl-substituted analogs 2–11 first, the data show that although some of them (2, 3, 6, 7, and 10) retain activity as inhibitors of RANTES-induced migration, none of them offer a distinct advantage in potency over cosalane, and four of the analogs (4, 5, 8, and 9) were inactive. Of the three boronic acid derivatives 8–10, only the meta-substituted compound 9 was active, and the corresponding meta carboxy analog 2 and the meta nitro compound 7 were also active. Considering the fact that the active analogs all have similar potencies, it seems that the benzyl substituents do not contribute any structural elements that are recognized by the receptor, although some of the substituents are simply not tolerated.

Of the amino acid derivatives, only the glycine conjugate 12 and the methionine derivative 15 retained activity, while the aspartic acid analog 13, the glutamic acid congener 14, and the phenylalanine compound 16 were inactive. Although the glycine derivative 12 was slightly more potent than cosalane with respect to RANTES-induced monocyte migration, it was less potent as an inhibitor of CCR1/HEK transfectant migration.

EXAMPLES 3 AND 4

Effect of a Cosalane Analog on MCP-4-induced Monocyte Migration and Eoxtaxin-induced Migration of Human Embryonic Kidney Cells Transfected to Express the CCR$_3$ Receptor Although MCP-4 is known to bind to CCR2 and CCR3, fresh primary human monocytes only express high levels of CCR2. Thus, FIG. 3 demonstrates the ability of compounds 1, 2 and 3 to block MCP-4/CCR2-mediated monocyte migration.

Figure 3:
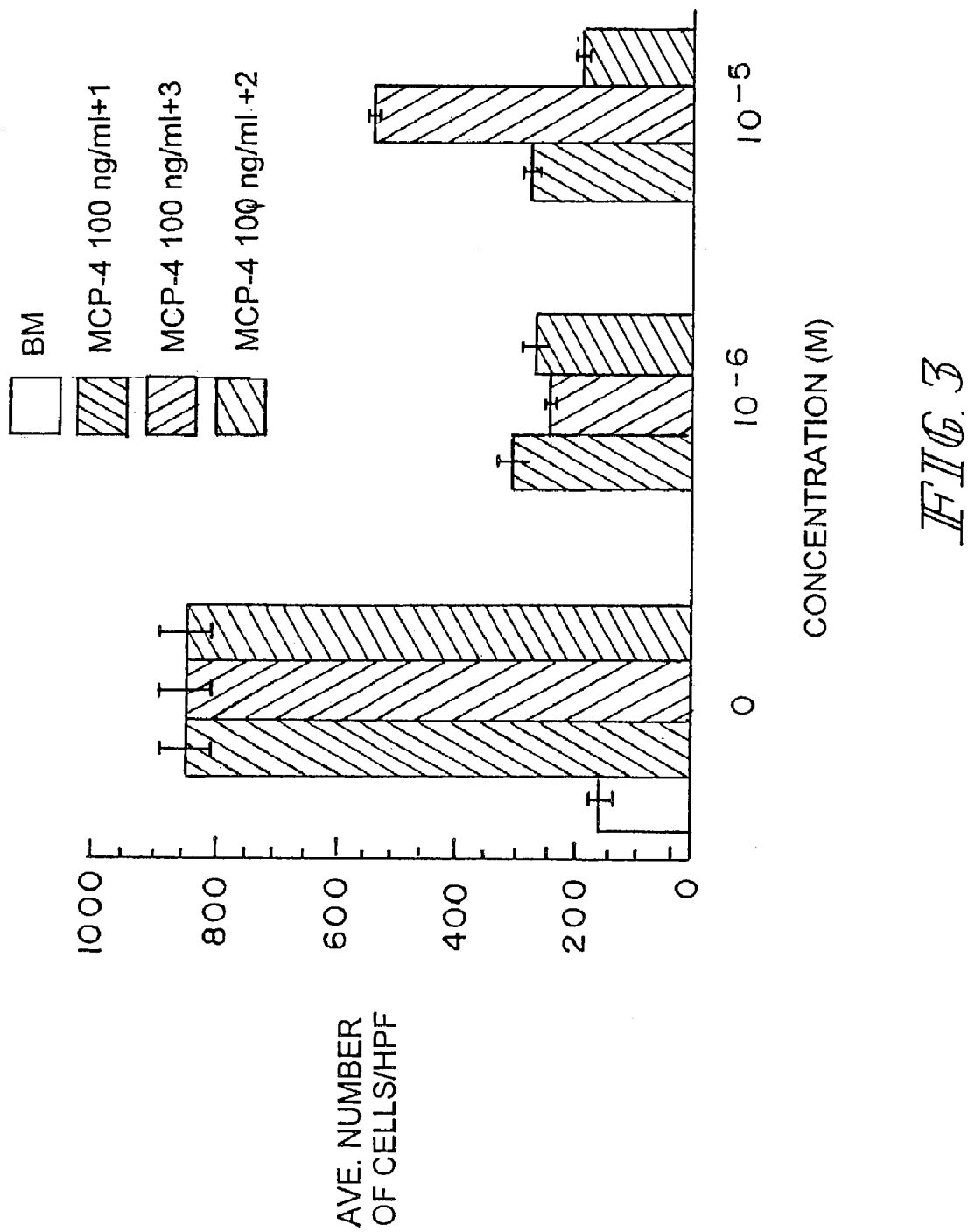
FIG. 3 is a bar graph depicting the effect of cosalane analogs on MCP-4-induced human monocyte migration as described in Example 3. BM, binding media; HPF, high powered field.
Figure 4:
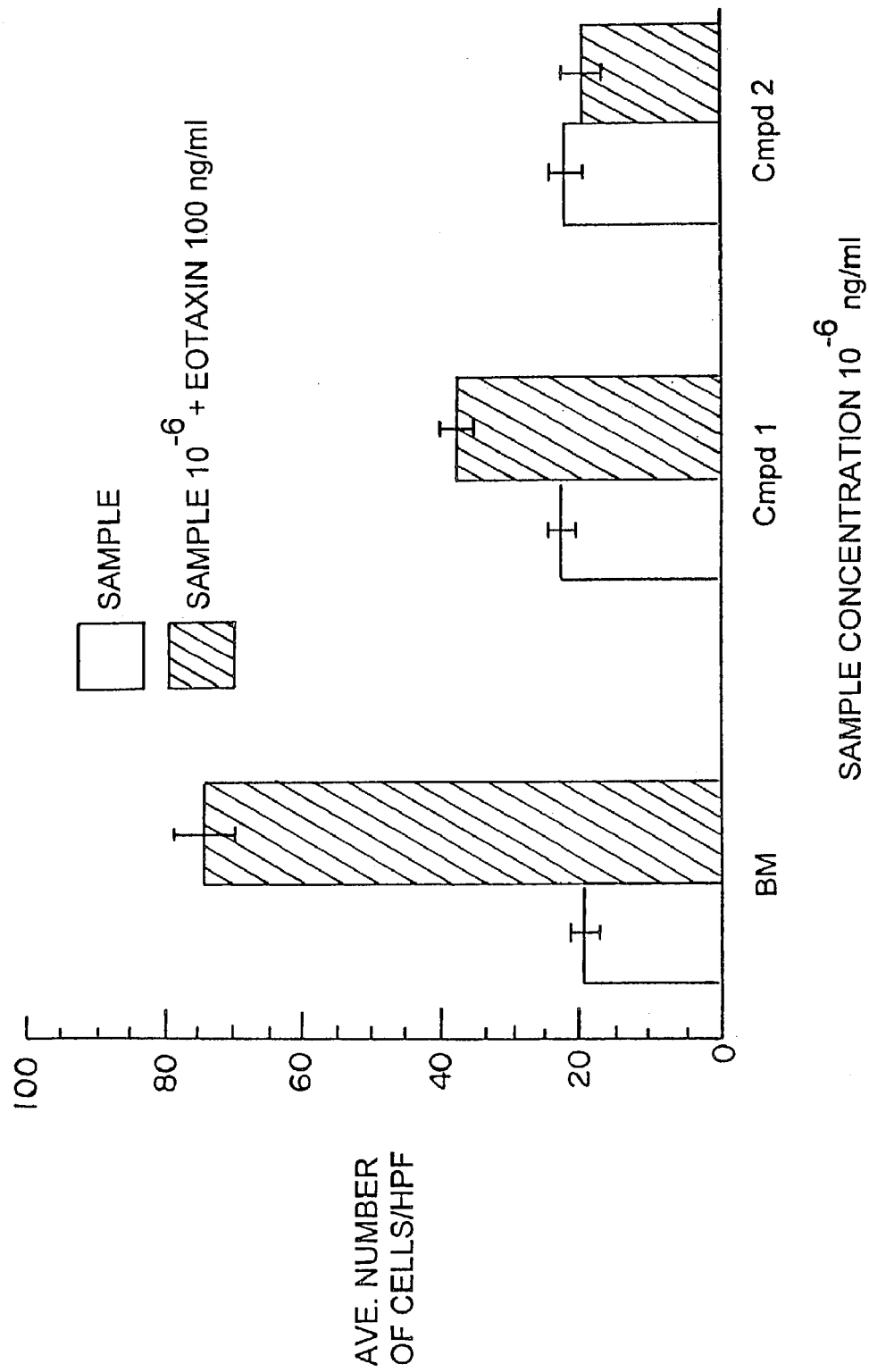
FIG. 4 represents a bar graph depicting the effect of cosalane and a cosalane analog on eotaxin-induced CCR3/HEK-293 cell migration as described in Example 4. CCR3 is a receptor for the CC class of chemokines. BM, binding media; HPF, high powered field.
Figure 5:
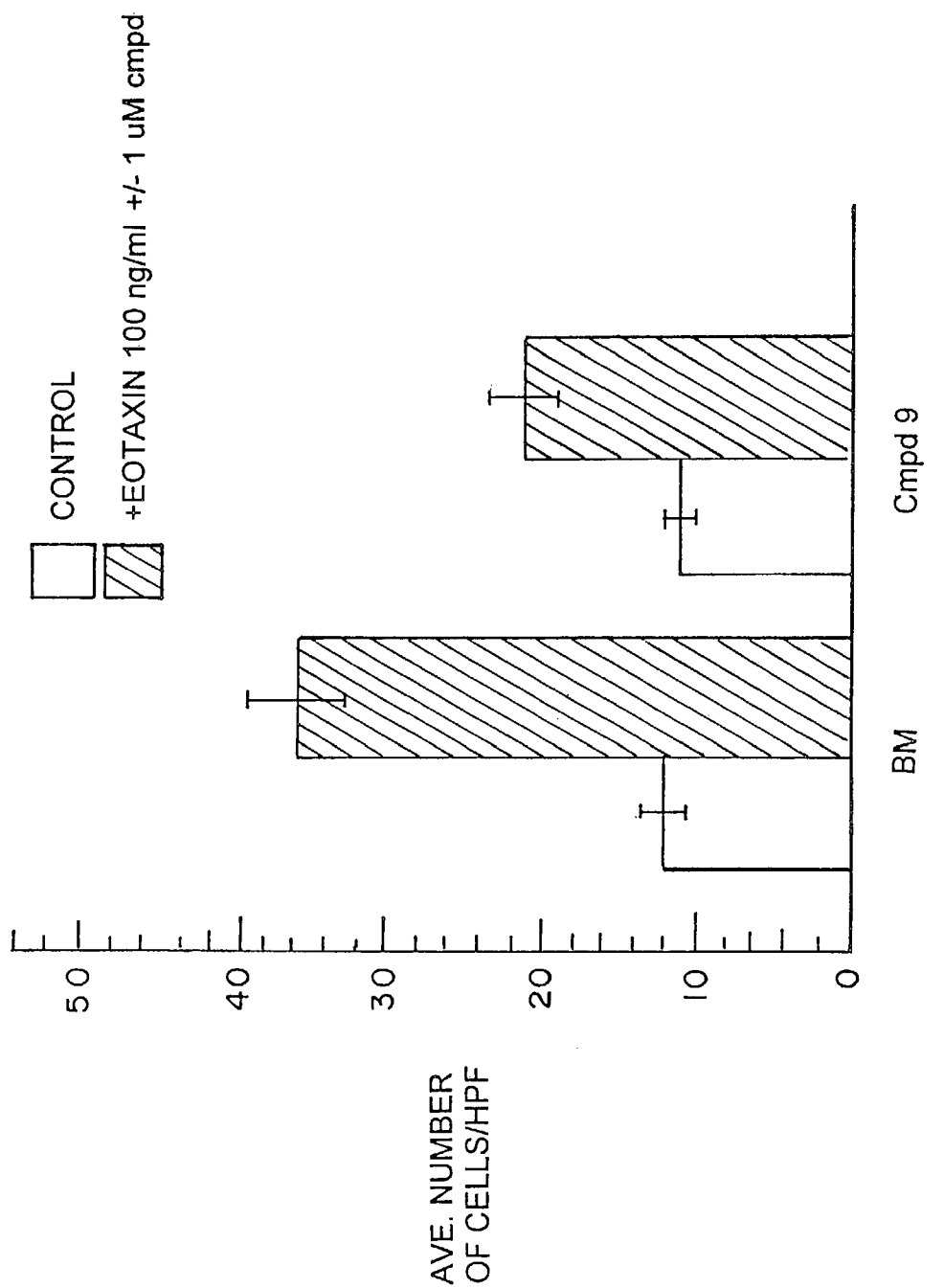
FIG. 5 represents a bar graph depicting the effect of cosalane and a cosalane analog on eotaxin-induced CCR3/HEK-293 cell migration as described in Example 4. BM, binding media; HPF, high powered field.

Additionally, as seen in FIGS. 3 and 4, cosalane compounds 1, 2 and 9 inhibit the function of CCL11 (eotaxin) interaction with CCR$_3$.

EXAMPLE 5

Figure 6:
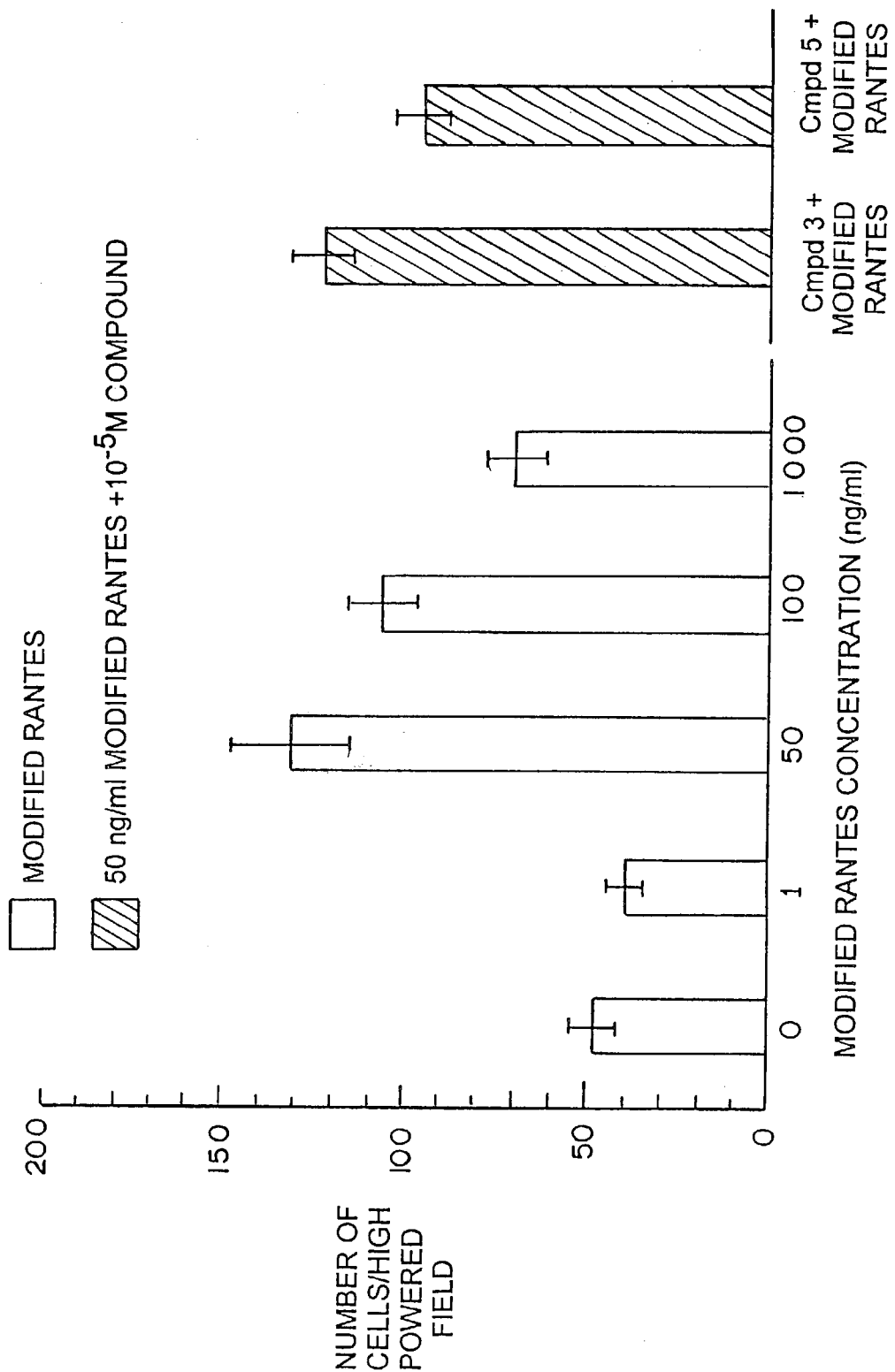
FIG. 6 is a bar graph depicting the effect of amino group modification of RANTES on the ability of cosalane analogs to inhibit RANTES-induced myeloid cell migration as described in Example 5.

Effect of Chemical Modification of RANTES on RANTES-induced Monocyte Migration in the Presence of Cosalane or Analogs Thereof In order to gain some insight into the possible mechanism of action of the cosalanes as inhibitors of the RANTES/CCR1 interaction, RANTES (10 μL of a 1 μg/mL solution) was acetylated with sulfo-N-hydroxysuccinimide acetate (8 μL of a 1 μg/μL solution made in 10 mM sodium acetate buffer, pH 4.0, and then diluted with 2 μL of 10 mM sodium acetate buffer, pH 4.0) at room temperature for 30 min. The ability of the modified RANTES to attract monocytes in the presence of 10 μM cosalane or cosalane congeners 3 and 5 were examined and the results are shown in FIG. 6. Although the acetylated protein in the concentration range of 50–1000 ng/mL retained the ability to attract monocytes, the activity of the modified RANTES was not inhibited by either 30 μM cosalane or by 10 μM compound 3. In regard to the compound 5/modified RANTES treated samples, there is a decrease in the average number of cells, however the standard deviation bars are overlapping and statistical analysis shows that there is no statistical difference between this sample and 50 ng/ml RANTES alone. Although not being limited by theory, this data suggests that cosalane and its analog 3 may be binding to RANTES and not to CCR1.

EXAMPLE 6

Synthesis of Amino Acid Conjugates of Cosalane

Amino acid derivatives having the following structure were synthesized:

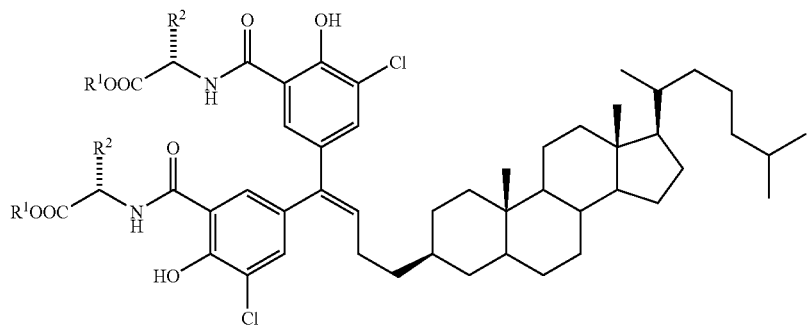

wherein, for compound B, $R^1$ is t-Bu, $R^2$ is H; compound C, R' is H, $R^2$ is H; compound E, $R^1$ is $CH_3$, $R^2$ is $CH_2CH(CH_3)_2$; compound G, $R^1$ is H, $R^2$ is $CH_2CH(CH_3)_2$; compound H, $R^1$ is $CH_3$, $R^2$ is $CH_2Ph$; compound I, $R^1$ is H, $R^2$ is $CH_2Ph$, compound J, $R^1$ is t-Bu, $R^2$ is $CH_2Coot$-Bu; compound K, $R^1$ is H, $R^2$ is $CH_2COOH$; compound L, $R^1$ is t-Bu, $R^2$ is $CH_2CH_2COOt$-Bu, compound M, $R^1$ is H, $R^2$ is $CH_2CH_2COOH$;

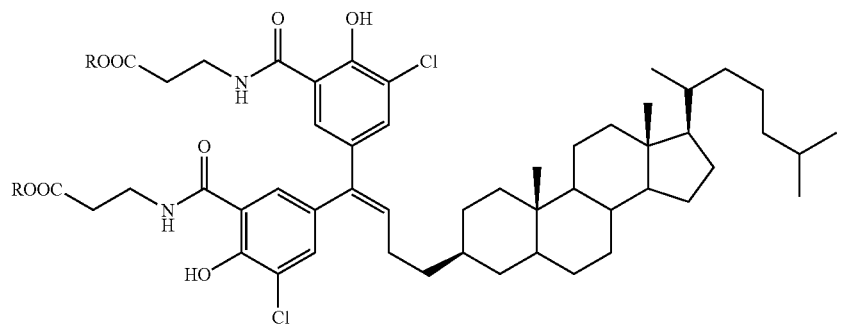

wherein, for compound D, R is ethyl and for compound E, R is H;

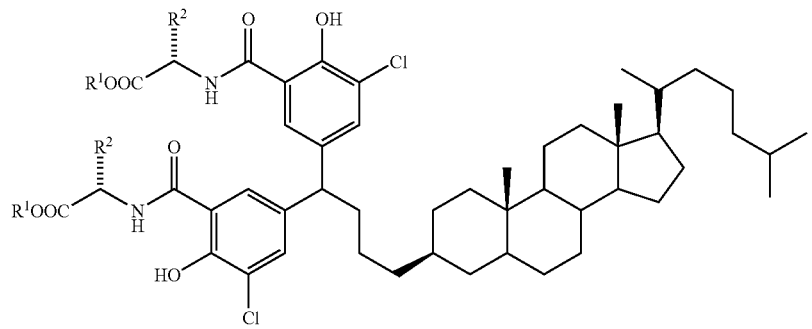

wherein, for compound N, $R^1$ is t-butyl, $R^2$ is hydrogen; compound O, $R^1$ is H, $R^2$ is H; compound P, $R^1$ is t-butyl, $R^2$ is $CH_2CH_2COO$-t-butyl; compound Q, $R^1$ is H, $R^2$ is $CH_2CH_2COOH$.

Briefly, in synthesizing the amino acid derivatives of cosalane, amide bond formation during the coupling of cosalane to the amino acid derivatives were performed by reacting the hydrochloride salts of the amino acids with cosalane or dihydrocosalane in the presence of BOP and triethylamine in tetrahydrofuran. The leucine and phenylalanine derivatives were synthesized by coupling cosalane with the methyl esters of leucine and phenylalanine to afford protected intermediates. Hydrolysis of the methyl esters of the intermediates yielded the desired analogs. The aspartic acid derivative and the glutamic acid derivative were synthesized by reaction of cosalane with the corresponding di-tert-butyl esters of the amino acids, followed by saponification of the four tert-butyl ester groups. The glycine derivative of cosalane was similarly prepared by coupling cosalane to the tert-butyl ester of glycine to afford an ester intermediate which may be hydrolyzed. The β-alanine derivative was prepared by coupling cosalane to β-alanine ethyl ester, resulting in an ester intermediate, followed by hydrolysis of the ester groups. The dihydroanalogs O and Q were prepared by coupling dihydrocosalane with the corresponding di-tert-butyl esters of glycine and glutamic aid to afford N and P, followed by hydrolysis.

CONCLUSIONS

The involvement of CCR1, RANTES, and MIP1-α in multiple sclerosis and rheumatoid arthritis has stimulated interest in the design and synthesis of small molecule CCR1 antagonists. Recent studies published by Ng et al. and by Liang et al. have documented a series of CCR1 antagonists that inhibit the binding of MIP1-α, MCP-3, and RANTES (17,18). In contrast, the present series of compounds inhibit the RANTES-CCR1 interaction, but not the MIP-α interaction, and are therefore complementary in activity to the prior series of CCR1 antagonists. Hypothetically, the difference in selectivity between the present series and the prior series could reflect binding to RANTES versus binding to CCR1, respectively.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

REFERENCES

1. Cushman, M. et al. (1994) *J. Med. Chem.* 37:3040–3050.
2. Choe, H. et al. (1996) *Cell* 85:1135–1148.
3. Dean, M. et al. (1996) *Science* 273:1856–1862.
4. Doranz, B. J. et all (1996) *Science* 272:1955–1958.
6. Deng, H., et al. (1996) *Nature* 381:661–666.
7. Dragic, T., et al. (1996) *Nature* 381:667–673.
8. Zlotnik, A. et al., (1999) *Crit. Rev. Immunol.* 19:1–47.
9. Gangur, V., et al. (2000) Ann. Allergy Asthma, Immunol. 84:569–581.
10. Robinson, D. S. et al., (1999) Lung Biol. Health Dis. 136:19–41.
11. Moore, B. B., et al. (1998). Angiogenesis 2:123–134.
12. Cushman, M., et al. (1998) *Bioorg. Med. Chem. Lett.* 8:833–836.
13. Cushman, M., et al. (1999) *J. Med. Chem.* 42:1767–1777.
14. Paul, G. C., et al. (2000) *Bioorg. Med. Chem. Lett.* 10:2149–2152.
15. Murata, M., et al. (1997) *J. Org. Chem.* 62:6458–6459.
16. Santhosh, K. C., et al. (2000) (in press).
17. Ng, H. P, et al. (1999) *J. Med. Chem.* 42:4680–4694.
18. Liang, M., et al. (2000) *J. Biol. Chem.* 275:19000–19008.

What is claimed is:

1. A method of inhibiting effective binding of a chemokine to its cellular receptor, comprising contacting a cellular population with an effective amount of a compound having the following structure:

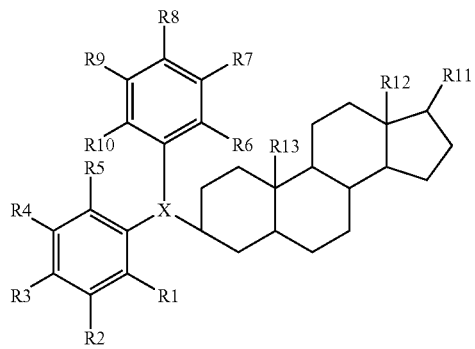

wherein:
$R_1$ to $R_{11}$ are independently H, a halogen, hydroxy, amino, alkoxy having 1 to 5 carbon atoms, benzoyloxy, $R_{14}C(O)O$, where $R_{14}$ is H or $C_1$–$C_5$ alkyl; COOH or a salt thereof, $SO_3H$ or a salt thereof, $PO_3H_2$ or a salt thereof, $C_1$–$C_{24}$ alkyl, $COOR_{15}$ where $R_{15}$ is aryl or $C_1$–$C_5$ alkyl; $SO_3R_{16}$, where $R_{16}$ is aryl or $C_1$–$C_5$ alkyl; $C(O)NR_{17}R_{18}$ where $R_{17}$ and $R_{18}$ are each independently H, $C_1$–$C_5$ alkyl, aryl, or hydroxy; $SO_2NR_{19}R_{20}$ where $R_{19}$ and $R_{20}$ are each independently H, $C_1$–$C_5$ alkyl, or aryl; $SR_{21}$ where $R_{21}$ is $C_1$–$C_5$ alkyl or aryl; $SCH_2R_{25}$, where $R_{25}$ is aryl; $SC(O)R_{21}$ where $R_{21}$ is as defined above; $NR_{22}R_{23}$ where $R_{22}$ and $R_{23}$ are each independently H, $C_1$–$C_5$ alkyl, or aryl; NHC(O)—$R_{24}$, where $R_{24}$ is aryl optionally substituted with COOH or a salt thereof, or $C_1$–$C_7$ alkoxy; $O(CH_2)_n$—$R_{26}$—$R_{27}$, where n is 1 to 7, $R_{26}$ is aryl, $R_{27}$ is COOH or a salt thereof, $B(OH)_2$ or a salt thereof, nitro, $C_1$–$C_7$ alkoxy, or aryl wherein the aryl of $R_{27}$ is substituted with COOH or a salt thereof, $B(OH)_2$ or a salt thereof, nitro, or $C_1$–$C_7$ alkoxy; $OC(O)NHCH(R_{28})COOR_{29}$ or $C(O)NHCH(R_{28})COOR_{29}$, wherein $R_{28}$ is an amino acid side chain and $R_{29}$ is H or a $C_1$–$C_4$ alkyl;
$R_{12}$ and $R_{13}$ are $C_1$–$C_7$ alkyl;
X is a ($C_1$–$C_7$ alkylene) or ($C_1$–$C_7$ alkylene)C(O)NH;
or a pharmaceutically acceptable salt thereof.

2. The method of claim 1, wherein said cellular population comprises immune system cells.

3. The method of claim 1, wherein $R_1$, $R_5$, $R_6$, and $R_{10}$ are H, $R_2$ and $R_7$ are chlorine, $R_{11}$ is $CH(CH_3)(CH_2)_3CH(CH_3)_2$, $R_{12}$ and $R_{13}$ are methyl, and X is C=CH(CH$_2$)$_2$.

4. The method of claim 3, wherein $R_3$ and $R_8$ are hydroxy, and $R_4$ and $R_9$ are COOH or a salt thereof.

5. The method of claim 3, wherein $R_3$ and $R_8$ are $O(CH_2)_n$—$R_{26}$—$R_{27}$, where n is 1, $R_{26}$ is phenyl, $R_{27}$ is selected from the group consisting of aryl, nitro, COOH or a salt thereof, $B(OH)_2$ or a salt thereof, $C_1$–$C_7$ alkoxy, and combinations thereof, where the aryl of $R_{27}$ is optionally substituted with nitro, COOH or a salt thereof, $B(OH)_2$ or a salt thereof, $C_1$–$C_7$ alkoxy, or combinations thereof.

6. The method of claim 1, wherein $R_3$ and $R_8$ are hydroxy, and $R_4$ and $R_9$ are $C(O)NHCH(R_{28})COOH$, where $R_{28}$ is H, $CH_2CH(CH_3)_2$, $CH_2Ph$, $CH_2COOH$ or a salt thereof, or $CH_2CH_2COOH$ or a salt thereof.

7. The method of claim 1, wherein said chemokine is selected from the group consisting of a class CXC chemokine and a class CC chemokine.

8. The method of claim 1, wherein said class CC chemokine is RANTES.

9. The method of claim 7, wherein said class CC chemokine is selected from the group consisting of RANTES, MCP-1, MCP-2, MCP-3, MCP-4, eotaxin, MDC, TARC, and HCC-1.

10. The method of claim 7, wherein said class CXC chemokine is selected from the group consisting of PF4, IL-8, GRO-alpha, ENA-78, IP-10, BCA-1, ITAC, and SDF-1.

11. The method of claim 1, wherein chemokine-induced cellular chemotaxis is inhibited.

12. A method of treating an inflammatory disease, the method comprising administering to a patient a therapeutically effective amount of a compound, said amount being sufficient to inhibit binding of a chemokine to its cellular receptor, said compound having the following formula:

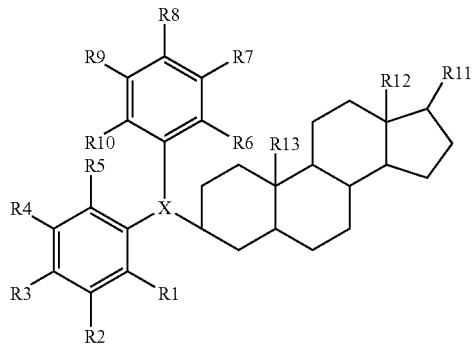

wherein

R$_1$ to R$_{11}$ are independently H, a halogen, hydroxy, amino, alkoxy having 1 to 5 carbon atoms, benzoyloxy, R$_{14}$C(O)O, where R$_{14}$ is H or C$_1$–C$_5$ alkyl; COOH or a salt thereof, SO$_3$H or a salt thereof, PO$_3$H$_2$ or a salt thereof, C$_1$–C$_{24}$ alkyl, COOR$_{15}$ where R$_{15}$ is aryl or C$_1$–C$_5$ alkyl; SO$_3$R$_{16}$, where R$_{16}$ is aryl or C$_1$–C$_5$ alkyl; C(O)NR$_{17}$R$_{18}$ where R$_{17}$ and R$_{18}$ are each independently H, C$_1$–C$_5$ alkyl, aryl, or hydroxy; SO$_2$NR$_{19}$R$_{20}$ where R$_{19}$ and R$_{20}$ are each independently H, C$_1$–C$_5$ alkyl, or aryl; SR$_{21}$ where R$_{21}$ is C$_1$–C$_5$ alkyl or aryl; SCH$_2$R$_{25}$, where R$_{25}$ is aryl; SC(O)R$_{21}$ where R$_{21}$ is as defined above; NR$_{22}$R$_{23}$ where R$_{22}$ and R$_{23}$ are each independently H, C$_1$–C$_5$ alkyl, or aryl; NHC(O)—R$_{24}$, where R$_{24}$ is aryl optionally substituted with COOH or a salt thereof, or C$_1$–C$_7$ alkoxy; O(CH$_2$)$_n$—R$_{26}$—R$_{27}$, where n is 1 to 7, R$_{26}$ is aryl, R$_{27}$ is COOH or a salt thereof, B(OH)$_2$ or a salt thereof, nitro, C$_1$–C$_7$ alkoxy, or aryl where the aryl of R$_{27}$ is substituted with COOH or a salt thereof, B(OH)$_2$ or a salt thereof, nitro, or C$_1$–C$_7$ alkoxy; OC(O)NHCH(R$_{28}$)COOR$_{29}$ or C(O)NHCH(R$_{28}$)COOR$_{29}$, where R$_{28}$ is an amino acid side chain and R$_{29}$ is H or a C$_1$–C$_4$ alkyl;

R$_{12}$ and R$_{13}$ are C$_1$–C$_7$ alkyl;

X is a (C$_1$–C$_7$ alkylene) or (C$_1$–C$_7$ alkylene)C(O)NH; or a pharmaceutically acceptable salt thereof.

13. The method of claim 12, wherein said cellular population comprises immune system cells.

14. The method of claim 12, wherein R$_1$, R$_5$, R$_6$, and R$_{10}$ are H, R$_2$ and R$_7$ are chlorine, R$_{11}$ is CH(CH$_3$)(CH$_2$)$_3$CH(CH$_3$)$_2$, R$_{12}$ and R$_{13}$ are methyl, and X is C=CH(CH$_2$)$_2$.

15. The method of claim 14, wherein R$_3$ and R$_8$ are hydroxy, and R$_4$ and R$_9$ are COOH or a salt thereof.

16. The method of claim 14, wherein R$_3$ and R$_8$ are O(CH$_2$)$_n$—R$_{26}$—R$_{27}$, where n is 1, R$_{26}$ is phenyl, R$_{27}$ is selected from the group consisting of aryl, nitro, COOH or a salt thereof, B(OH)$_2$ or a salt thereof, C$_1$–C$_7$ alkoxy, and combinations thereof, where the aryl of R$_{27}$ is optionally substituted with nitro, COOH or a salt thereof, B(OH)$_2$ or a salt thereof, C$_1$–C$_7$ alkoxy, or combinations thereof.

17. The method of claim 14, wherein R$_3$ and R$_8$ are hydroxy, and R$_4$ and R$_9$ are C(O)NHCH(R$_{28}$)COOH, where R$_{28}$ is H, CH$_2$CH(CH$_3$)$_2$, CH$_2$Ph, CH$_2$COOH or a salt thereof, or CH$_2$CH$_2$COOH or a salt thereof.

18. The method of claim 12, wherein said chemokine is selected from the group consisting of a class CXC chemokine and a class CC chemokine.

19. The method of claim 18, wherein said class CC chemokine is RANTES.

20. The method of claim 18, wherein said class CC chemokine is selected from the group consisting of RANTES, MCP-1, MCP-2, MCP-3, MCP-4, eotaxin, MDC, TARC, and HCC-1.

21. The method of claim 18, wherein said class CXC chemokine is selected from the group consisting of PF4, IL-8, GRO-alpha, ENA-78, IP-10, BCA-1, ITAC, and SDF-1.

22. A compound having the formula:

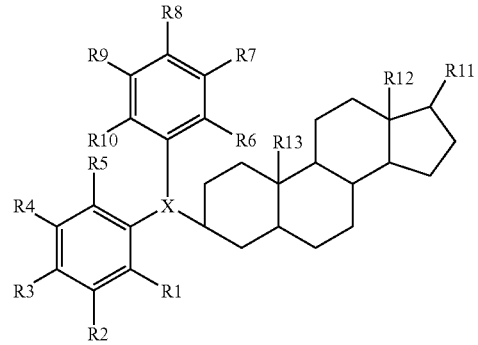

wherein

R$_1$ to R$_{11}$ are independently H, a halogen, hydroxy, amino, alkoxy having 1 to 5 carbon atoms, benzoyloxy, R$_{14}$C(O)O, where R$_{14}$ is H or C$_1$–C$_5$ alkyl; COOH or a salt thereof, SO$_3$H or a salt thereof, PO$_3$H$_2$ or a salt thereof, C$_1$–C$_{24}$ alkyl, COOR$_{15}$ where R$_{15}$ is aryl or C$_1$–C$_5$ alkyl; SO$_3$R$_{16}$, where R$_{16}$ is aryl or C$_1$–C$_5$ alkyl; C(O)NR$_{17}$R$_{18}$ where R$_{17}$ and R$_{18}$ are each independently H, C$_1$–C$_5$ alkyl, aryl, or hydroxy; SO$_2$NR$_{19}$R$_{20}$ where R$_{19}$ and R$_{20}$ are each independently H, C$_1$–C$_5$ alkyl, or aryl; SR$_{21}$ where R$_{21}$ is C$_1$–C$_5$ alkyl or aryl; SCH$_2$R$_{25}$, where R$_{25}$ is aryl; SC(O)R$_{21}$ where R$_{21}$ is as defined above; NR$_{22}$R$_{23}$ where R$_{22}$ and R$_{23}$ are each independently H, C$_1$–C$_5$ alkyl, or aryl; NHC(O)—R$_{24}$, where R$_{24}$ is aryl optionally substituted with COOH or a salt thereof, or C$_1$–C$_7$ alkoxy; O(CH$_2$)$_n$—R$_{26}$—R$_{27}$, where n is 1 to 7, R$_{26}$ is aryl, R$_{27}$ is COOH or a salt thereof, B(OH)$_2$ or a salt thereof, nitro, C$_1$–C$_7$ alkoxy, or aryl wherein the aryl of R$_{27}$ is substituted with COOH or a salt thereof, B(OH)$_2$ or a salt thereof, nitro, or C$_1$–C$_7$ alkoxy; OC(O)NHCH(R$_{28}$)COOR$_{29}$ or C(O)NHCH(R$_{28}$)COOR$_{29}$, where R$_{28}$ is an amino acid side chain and R$_{29}$ is H or a C$_1$–C$_4$ alkyl;

R$_{12}$ and R$_{13}$ are C$_1$–C$_7$ alkyl;

X is a (C$_1$–C$_7$ alkylene) or (C$_1$–C$_7$ alkylene)C(O)NH; or a pharmaceutically acceptable salt thereof;

provided that at least one of R$_4$ and R$_9$ is C(O)NHCH(R$_{28}$)COOR$_{29}$ or at least one of R$_3$ and R$_8$ is O(CH$_2$)$_n$—R$_{26}$—R$_{27}$.

23. The compound of claim 22, wherein at least one of R$_4$ and R$_9$ is C(O)NHCH(R$_{28}$)COOR$_{29}$, where R$_{28}$ is an amino acid side chain and R$_{29}$ is H or a C$_1$–C$_4$ alkyl.

24. The compound of claim 23, wherein R$_1$, R$_5$, R$_6$, and R$_{10}$ are H, R$_2$ and R$_7$ are chlorine, R$_{11}$ is CH(CH$_3$)(CH$_2$)$_3$CH(CH$_3$)$_2$, R$_{12}$ and R$_{13}$ are methyl, and X is C=CH(CH$_2$)$_2$.

25. The compound of claim 24, wherein R$_3$ and R$_8$ are hydroxy, and R$_4$ and R$_9$ are C(O)NHCH(R$_{28}$)COOH, where R$_{28}$ is H, CH$_2$CH(CH$_3$)$_2$, CH$_2$Ph, CH$_2$COOH or a salt thereof, and CH$_2$CH$_2$COOH or a salt thereof.

26. The compound of claim 22, wherein at least one of R$_3$ and R$_8$ is O(CH$_2$)$_n$—R$_{26}$—R$_{27}$, where n is 1 to 7, R$_{26}$ is aryl, R$_{27}$ is COOH or a salt thereof, B(OH)$_2$ or a salt thereof, nitro, C$_1$–C$_7$ alkoxy, or aryl where the aryl of R$_{27}$ is substituted with COOH or a salt thereof, B(OH)$_2$ or a salt thereof, nitro, or C$_1$–C$_7$ alkoxy.

27. The compound of claim 26, wherein R$_1$, R$_5$, R$_6$, and R$_{10}$ are H, R$_2$ and R$_7$ are chlorine, R$_{11}$ is CH(CH$_3$)(CH$_2$)$_3$CH(CH$_3$)$_2$, R$_{12}$ and R$_{13}$ are methyl, and X is C=CH(CH$_2$)$_2$.

28. The compound of claim 27, wherein $R_3$ and $R_8$ are $O(CH_2)_n-R_{26}-R_{27}$, where n is 1, $R_{26}$ is phenyl, $R_{27}$ is selected from the group consisting of aryl, nitro, COOH or a salt thereof, $B(OH)_2$ or a salt thereof, $C_1-C_7$ alkoxy, and combinations thereof, where the aryl of $R_{27}$ is optionally substituted with nitro, COOH or a salt thereof, $B(OH)_2$ or a salt thereof, $C_1-C_7$ alkoxy, or combinations thereof.

29. A pharmaceutical composition comprising a compound according to claim 22 and a pharmaceutically acceptable carrier, excipient, or diluent therefor.

30. The method of claim 5, wherein the contacting step includes contacting the cellular population with an effective amount of the compound where $R_4$ and $R_9$ are COOH or a salt thereof, and $R_{27}$ is COOH or a salt thereof.

31. The method of claim 16, wherein administering step includes administering to a patient a therapeutically effective amount of the compound where $R_4$ and $R_9$ are COOH or a salt thereof, and $R_{27}$ is COOH or a salt thereof.

32. The compound of claim 28, wherein $R_4$ and $R_9$ are COOH or a salt thereof, and $R_{27}$ is COOH or a salt thereof.

* * * * *